US010538554B2

(12) United States Patent
Mohamed Ibrahim

(10) Patent No.: US 10,538,554 B2
(45) Date of Patent: Jan. 21, 2020

(54) PEPTIDES AND USES THEREFOR AS ANTIVIRAL AGENTS

(71) Applicant: VIRAMATIX SDN BHD, Kuala Lumpur (MY)

(72) Inventor: Mohamed Rajik Mohamed Ibrahim, Kuala Lumpur (MY)

(73) Assignee: VIRAMATIX SDN BHD, Kuala Lumpur (MY)

( * ) Notice: Subject to any disclaimer, the term of this patent is extended or adjusted under 35 U.S.C. 154(b) by 0 days.

(21) Appl. No.: 15/778,822

(22) PCT Filed: Nov. 28, 2016

(86) PCT No.: PCT/IB2016/057146
§ 371 (c)(1),
(2) Date: May 24, 2018

(87) PCT Pub. No.: WO2017/090010
PCT Pub. Date: Jun. 1, 2017

(65) Prior Publication Data
US 2018/0346516 A1    Dec. 6, 2018

Related U.S. Application Data

(60) Provisional application No. 62/425,913, filed on Nov. 23, 2016, provisional application No. 62/335,201, filed on May 12, 2016.

(30) Foreign Application Priority Data

Nov. 27, 2015    (MY) ................ 2015002751

(51) Int. Cl.
| | | |
|---|---|---|
| *C07K 7/06* | (2006.01) | |
| *C07K 7/08* | (2006.01) | |
| *C07K 7/64* | (2006.01) | |
| *A61P 31/16* | (2006.01) | |
| *A61K 38/00* | (2006.01) | |

(52) U.S. Cl.
CPC .............. *C07K 7/06* (2013.01); *A61P 31/16* (2018.01); *C07K 7/08* (2013.01); *C07K 7/64* (2013.01); *A61K 38/00* (2013.01); *C07K 2319/00* (2013.01)

(58) Field of Classification Search
CPC ..... A61K 38/00; A61P 31/16; C07K 2319/00; C07K 7/06; C07K 7/08; C07K 7/64
See application file for complete search history.

(56) References Cited

U.S. PATENT DOCUMENTS

2013/0190228 A1    7/2013    Schultz-Cherry
2013/0205416 A1    8/2013    Nash

FOREIGN PATENT DOCUMENTS

| WO | 2006/128294 | 12/2006 | |
|---|---|---|---|
| WO | 2007/041487 | 4/2007 | |
| WO | 2009/040529 | 4/2009 | |
| WO | WO2018217075 | * 11/2018 | ............. A61K 38/00 |

OTHER PUBLICATIONS

PCT Search Report prepared for PCT/IB2016/057146, dated Feb. 27, 2017.
Jaishankar, D., et al, "Characterisation of Proteolytically Stable D-Peptide That Surpresses Herpes Simplex Virus 1 Infection: Implications for the Development of Entry-Based Antiviral Therapy", Journal of Virology, 2015, 89(3), 1932-8.
Rajik, M., Jahanshiri, F., Omar, A. R., Ideris, A., Hassan, S. S., & Yusoff, K. (2009). Identification and characterisation of a novel anti-viral peptide against avian influenza virus H9N2. Virology journal, 6(1), 74.
Ben-Yedidia, T., Beignon, A. S., Partidos, C. D., Muller, S., & Arnon, R. (2002). A retro-inverso peptide analogue of influenza virus hemagglutinin B-cell epitope 91-108 induces a strong mucosal and systemic immune response and confers protection in mice after intranasal immunization. Molecular immunology, 39(5-6), 323-331.
Nair, D. T., Kaur, K. J., Singh, K., Mukherjee, P., Rajagopal, D., George, A., . . . & Salunke, D. M. (2003). Mimicry of native peptide antigens by the corresponding retro-inverso analogs is dependent on their intrinsic structure and interaction propensities. The Journal of Immunology, 170(3), 1362-1373.
Zhong, Y., Cai, J., Zhang, C., Xing, X., Qin, E., He, J., . . . & Song, H. (2011). Mimotopes selected with neutralizing antibodies against multiple subtypes of influenza A. Virology journal, 8(1), 542.

* cited by examiner

*Primary Examiner* — Marcela M Cordero Garcia
(74) *Attorney, Agent, or Firm* — Brannon Sowers & Cracraft PC

(57) ABSTRACT

Peptides with anti-influenza properties are disclosed herein. The peptides include dextro (D) or a mixture of dextro/levo (L)-amino acids, possess anti-influenza properties against multiple types of human influenza viruses along with the types which infect animals and birds and are useful as pharmaceutical compositions for the treatment or prevention of influenza virus infections.

20 Claims, 9 Drawing Sheets

Specification includes a Sequence Listing.

Figure 1A: Effect of PSP III B5 and PSP IV A5 against H1N1 *in vitro*

Figure 1B: Effect of PSP III B5 and PSP IV A5 against H3N2 *in vitro*

Figure 1C: Effect of PSP III B5 and PSP IV A5 against 2009 pandemic virus *in vitro*

Figure 1D: Effect of PSP III B5 and PSP IV A5 against H9N2 *in vitro*

Figure 1E: Effect of PSP III B5 and PSP IV A5 against H3N8 *in vitro*
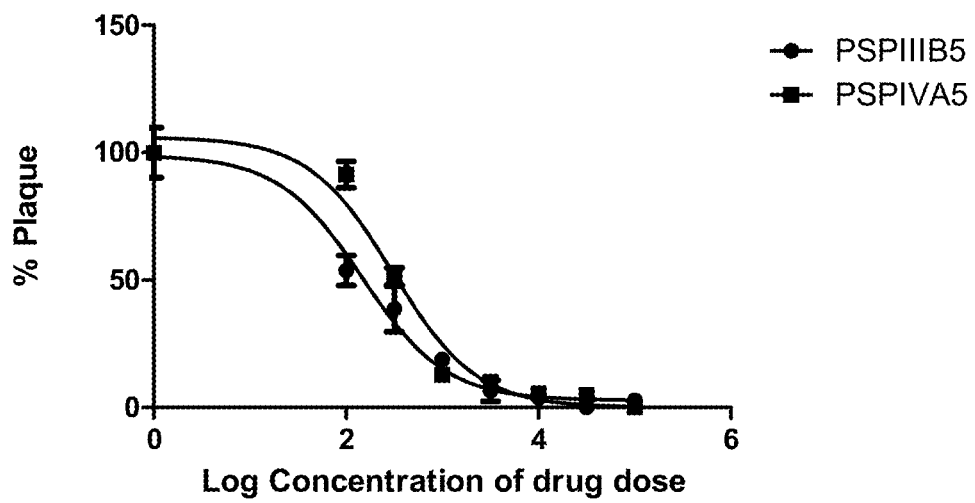
Figure 1F: Effect of PSP III B5 and PSP IV A5 against H5N Figure 2: Effect of Oseltamivir acid and PSP IV A5 against H1N1 PR8 *in vitro*

Figure 3: Effect of PSPV A19 against H1N1 PR8 *in vitro*

Figure 4: Effect of PSP VI A1 against H1N1 PR8 *in vitro*

PSP VI A 1

Figure 5: Effect of PSP IV A17 against Mouse adapted H1N1 PR8 *in vivo*

Figure 6A: Cytotoxic effects of anti-viral peptides in human hepatocytes
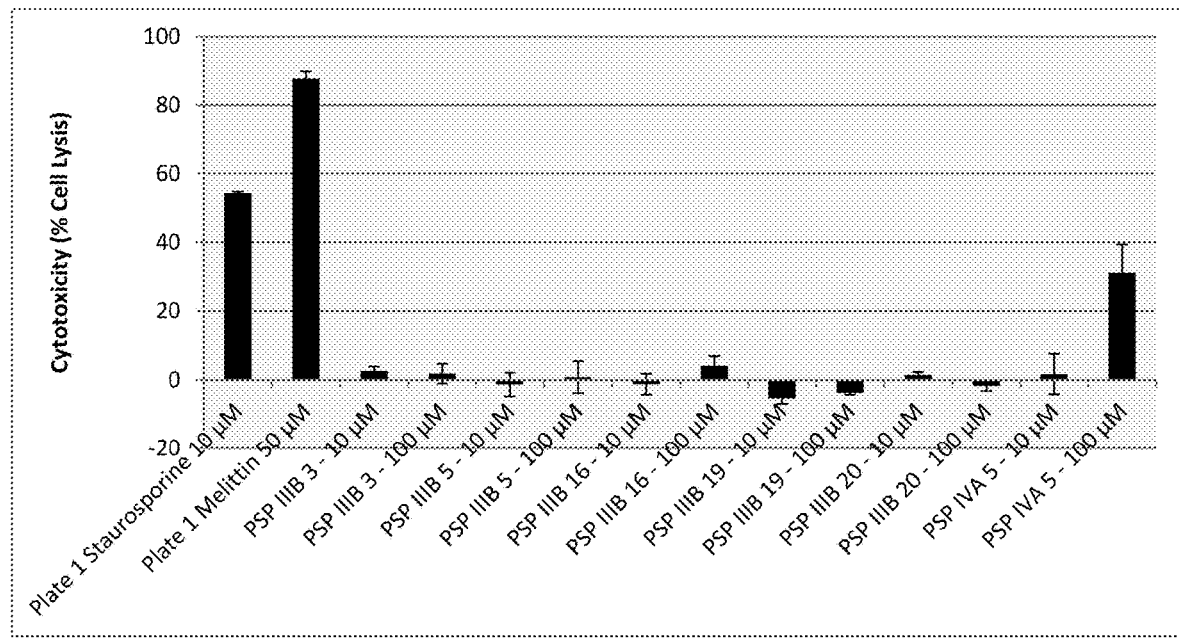
Figure 6B: Cytotoxic effects of anti-viral peptides in human hepatocytes
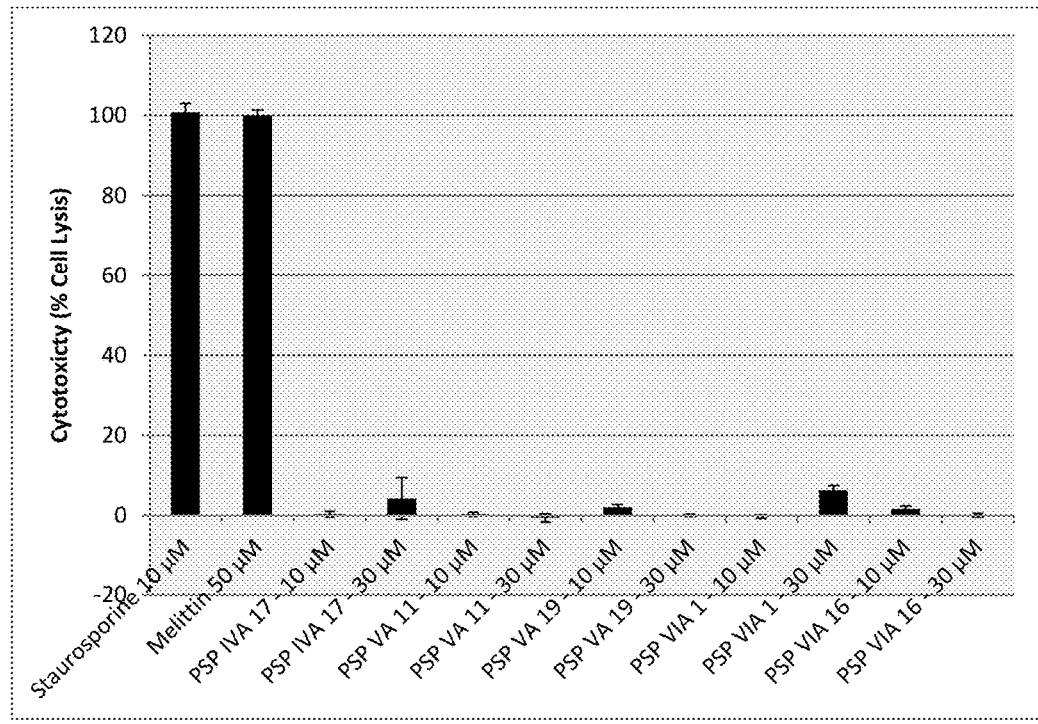

Figure 7A: Cytotoxic effects of anti-viral peptides PSP V A19 on MDCK & A549 cells Cytotoxicity of PSP VA 19 on MDCK cells Cytotoxicity of PSP VA 19 on A549 cells Control: No peptide treatment Figure 7B: Cytotoxic effects of anti-viral peptides PSP VI A1 on MDCK & A549 cells
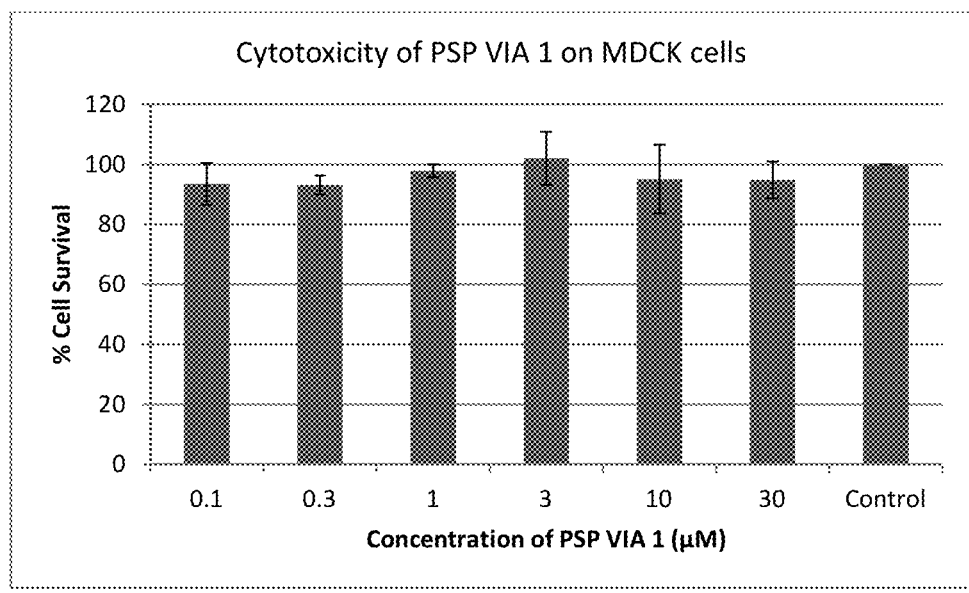
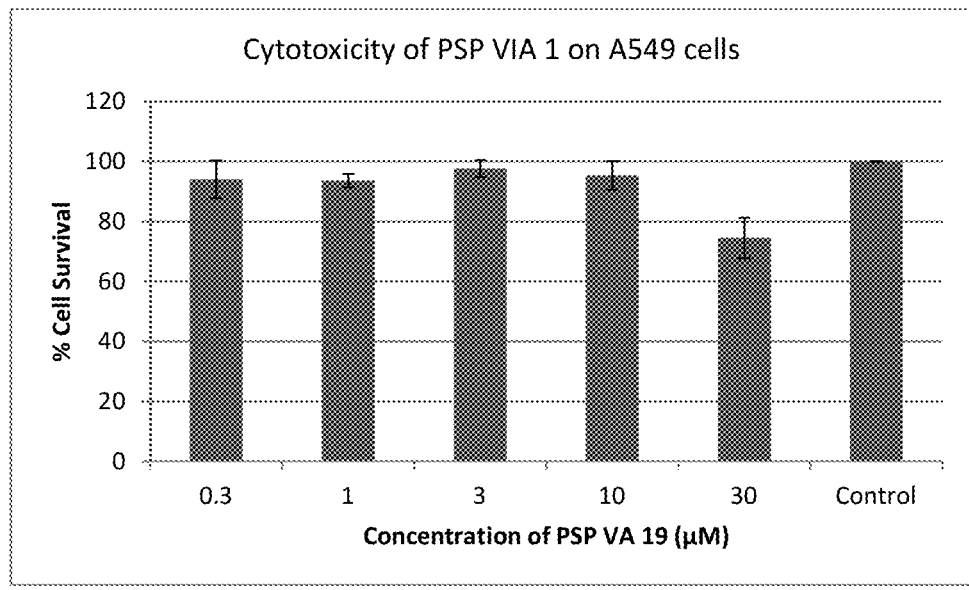
Control: No peptide treatment Figure 8: Hemolytic activities of different antiviral peptides at 30 μM concentration
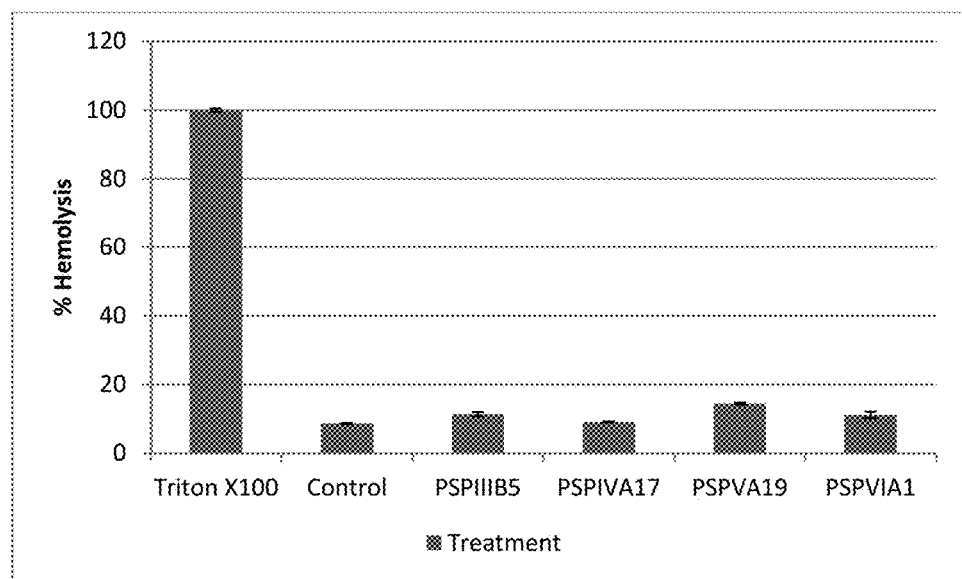
Control: No peptide treatment
Figure 9: Analysis of peptide treated HIN1 PR8 virus by electron microscopy
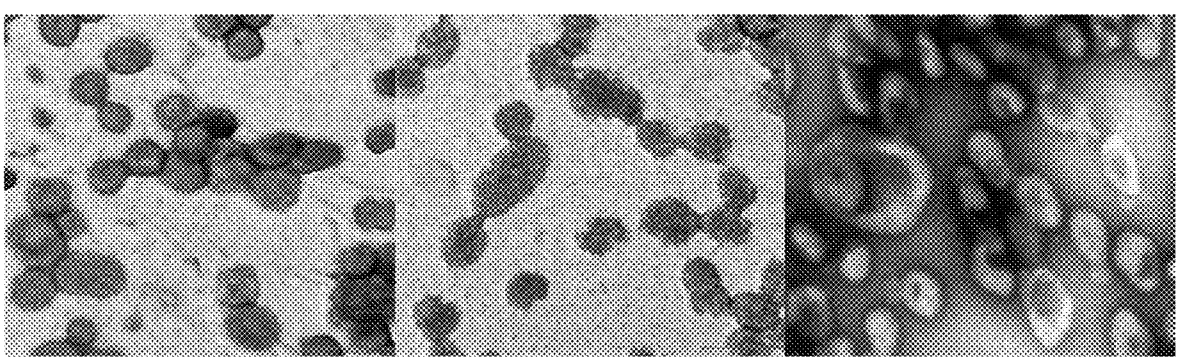
A B C

SEQUENCE LISTING

```
<160> NUMBER OF SEQ ID NOS: 158

<210> SEQ ID NO 1
<211> LENGTH: 7
<212> TYPE: PRT
<213> ORGANISM: Artificial Sequence
<220> FEATURE:
<223> OTHER INFORMATION: peptide

<400> SEQUENCE: 1

Asn Asp Phe Arg Ser Lys Thr
```

1               5

<210> SEQ ID NO 2
<211> LENGTH: 7
<212> TYPE: PRT
<213> ORGANISM: Artificial Sequence
<220> FEATURE:
<223> OTHER INFORMATION: peptide

<400> SEQUENCE: 2

Thr Lys Ser Arg Phe Asp Asn
1               5

<210> SEQ ID NO 3
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 3

Cys Asn Asp Phe Arg Ser Lys Thr Cys
1               5

<210> SEQ ID NO 4
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 4

Cys Thr Lys Ser Arg Phe Asp Asn Cys
1               5

<210> SEQ ID NO 5
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(5)
<223> OTHER INFORMATION: D-amino acids
<220> FEATURE:
<221> NAME/KEY: SITE
<222> LOCATION: (6)..(6)
<223> OTHER INFORMATION: any D/L amino acid
<220> FEATURE:
<221> NAME/KEY: SITE
<222> LOCATION: (7)..(7)
<223> OTHER INFORMATION: D-amino acid

<400> SEQUENCE: 5

Thr Lys Ser Arg Phe Xaa Asn
1               5

<210> SEQ ID NO 6
<211> LENGTH: 9
<212> TYPE: PRT
<213> ORGANISM: Artificial Sequence

```
<220> FEATURE:
<223> OTHER INFORMATION: peptide
<220> FEATURE:
<221> NAME/KEY: SITE
<222> LOCATION: (1)..(6)
<223> OTHER INFORMATION: D-amino acids
<220> FEATURE:
<221> NAME/KEY: SITE
<222> LOCATION: (7)..(7)
<223> OTHER INFORMATION: any D/L amino acid
<220> FEATURE:
<221> NAME/KEY: SITE
<222> LOCATION: (8)..(9)
<223> OTHER INFORMATION: D-amino acids

<400> SEQUENCE: 6

Cys Thr Lys Ser Arg Phe Xaa Asn Cys
1               5

<210> SEQ ID NO 7
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(1)
<223> OTHER INFORMATION: D-amino acid
<220> FEATURE:
<221> NAME/KEY: SITE
<222> LOCATION: (2)..(2)
<223> OTHER INFORMATION: any D/L amino acid
<220> FEATURE:
<221> NAME/KEY: SITE
<222> LOCATION: (3)..(7)
<223> OTHER INFORMATION: D-amino acids

<400> SEQUENCE: 7

Thr Xaa Ser Arg Phe Ile Asn
1               5

<210> SEQ ID NO 8
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(6)
<223> OTHER INFORMATION: D-amino acids
<220> FEATURE:
<221> NAME/KEY: SITE
<222> LOCATION: (7)..(7)
<223> OTHER INFORMATION: any D/L amino acid
<220> FEATURE:
<221> NAME/KEY: SITE
<222> LOCATION: (8)..(13)
<223> OTHER INFORMATION: D-amino acids

<400> SEQUENCE: 8

Arg Arg Lys Lys Cys Thr Xaa Ser Arg Phe Ile Asn Cys
1               5                   10

<210> SEQ ID NO 9
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
```

```
<222> LOCATION: (1)..(2)
<223> OTHER INFORMATION: D-amino acids
<220> FEATURE:
<221> NAME/KEY: SITE
<222> LOCATION: (3)..(3)
<223> OTHER INFORMATION: any D/L amino acid
<220> FEATURE:
<221> NAME/KEY: SITE
<222> LOCATION: (4)..(7)
<223> OTHER INFORMATION: D-amino acids

<400> SEQUENCE: 9

Thr Trp Xaa Arg Phe Ile Asn
 1               5

<210> SEQ ID NO 10
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(7)
<223> OTHER INFORMATION: D-amino acids
<220> FEATURE:
<221> NAME/KEY: SITE
<222> LOCATION: (8)..(8)
<223> OTHER INFORMATION: any D/L amino acid
<220> FEATURE:
<221> NAME/KEY: SITE
<222> LOCATION: (9)..(13)
<223> OTHER INFORMATION: D-amino acids

<400> SEQUENCE: 10

Arg Arg Lys Lys Cys Thr Trp Xaa Arg Phe Ile Asn Cys
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(3)
<223> OTHER INFORMATION: D-amino acids
<220> FEATURE:
<221> NAME/KEY: SITE
<222> LOCATION: (4)..(4)
<223> OTHER INFORMATION: any D/L amino acid
<220> FEATURE:
<221> NAME/KEY: SITE
<222> LOCATION: (5)..(7)
<223> OTHER INFORMATION: D-amino acids

<400> SEQUENCE: 11

Thr Trp Phe Xaa Phe Ile Asn
 1               5

<210> SEQ ID NO 12
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(8)
<223> OTHER INFORMATION: D-amino acids
<220> FEATURE:
<221> NAME/KEY: SITE
```

```
<222> LOCATION: (9)..(9)
<223> OTHER INFORMATION: any D/L amino acid
<220> FEATURE:
<221> NAME/KEY: SITE
<222> LOCATION: (10)..(13)
<223> OTHER INFORMATION: D-amino acids

<400> SEQUENCE: 12

Arg Arg Lys Lys Cys Thr Trp Phe Xaa Phe Ile Asn Cys
1               5                   10

<210> SEQ ID NO 13
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(1)
<223> OTHER INFORMATION: any D/L amino acid
<220> FEATURE:
<221> NAME/KEY: SITE
<222> LOCATION: (2)..(7)
<223> OTHER INFORMATION: D-amino acids

<400> SEQUENCE: 13

Xaa Trp Phe Thr Phe Ile Asn
1               5

<210> SEQ ID NO 14
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(5)
<223> OTHER INFORMATION: D-amino acids
<220> FEATURE:
<221> NAME/KEY: SITE
<222> LOCATION: (6)..(6)
<223> OTHER INFORMATION: any D/L amino acid
<220> FEATURE:
<221> NAME/KEY: SITE
<222> LOCATION: (7)..(13)
<223> OTHER INFORMATION: D-amino acids

<400> SEQUENCE: 14

Arg Arg Lys Lys Cys Xaa Trp Phe Thr Phe Ile Asn Cys
1               5                   10

<210> SEQ ID NO 15
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(6)
<223> OTHER INFORMATION: D-amino acids
<220> FEATURE:
<221> NAME/KEY: SITE
<222> LOCATION: (7)..(7)
<223> OTHER INFORMATION: any D/L amino acid

<400> SEQUENCE: 15

Trp Trp Phe Thr Phe Ile Xaa
1               5
```

<210> SEQ ID NO 16
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(11)
<223> OTHER INFORMATION: D-amino acids
<220> FEATURE:
<221> NAME/KEY: SITE
<222> LOCATION: (12)..(12)
<223> OTHER INFORMATION: any D/L amino acid
<220> FEATURE:
<221> NAME/KEY: SITE
<222> LOCATION: (13)..(13)
<223> OTHER INFORMATION: D-amino acid

<400> SEQUENCE: 16

Arg Arg Lys Lys Cys Trp Trp Phe Thr Phe Ile Xaa Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 17

Arg Arg Lys Lys Cys Thr Trp Ala Arg Phe Ile Asn Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 18

Arg Arg Lys Lys Cys Thr Trp Cys Arg Phe Ile Asn Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 19

Arg Arg Lys Lys Cys Thr Trp Asp Arg Phe Ile Asn Cys
1               5                   10

<210> SEQ ID NO 20
<211> LENGTH: 13

```
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 20

Arg Arg Lys Lys Cys Thr Trp Glu Arg Phe Ile Asn Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 21

Arg Arg Lys Lys Cys Thr Trp Phe Arg Phe Ile Asn Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids
<220> FEATURE:
<221> NAME/KEY: SITE
<222> LOCATION: (9)..(13)
<223> OTHER INFORMATION: D-amino acids

<400> SEQUENCE: 22

Arg Arg Lys Lys Cys Thr Trp Gly Arg Phe Ile Asn Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 23

Arg Arg Lys Lys Cys Thr Trp His Arg Phe Ile Asn Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: petpide
<220> FEATURE:
<221> NAME/KEY: SITE
<222> LOCATION: (5)..(13)
```

```
<223> OTHER INFORMATION: D-amino acids

<400> SEQUENCE: 24

Arg Arg Lys Lys Cys Thr Trp Ile Arg Phe Ile Asn Cys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 25

Arg Arg Lys Lys Cys Thr Trp Lys Arg Phe Ile Asn Cys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 26

Arg Arg Lys Lys Cys Thr Trp Leu Arg Phe Ile Asn Cys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 27

Arg Arg Lys Lys Cys Thr Trp Met Arg Phe Ile Asn Cys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 28

Arg Arg Lys Lys Cys Thr Trp Asn Arg Phe Ile Asn Cys
1               5                   10

<210> SEQ ID NO 29
<211> LENGTH: 13
<212> TYPE: PRT
```

```
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 29

Arg Arg Lys Lys Cys Thr Trp Pro Arg Phe Ile Asn Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 30

Arg Arg Lys Lys Cys Thr Trp Gln Arg Phe Ile Asn Cys
1               5                   10

<210> SEQ ID NO 31
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 31

Arg Arg Lys Lys Cys Thr Trp Arg Arg Phe Ile Asn Cys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 32

Arg Arg Lys Lys Cys Thr Trp Ser Arg Phe Ile Asn Cys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 33

Arg Arg Lys Lys Cys Thr Trp Thr Arg Phe Ile Asn Cys
```

<210> SEQ ID NO 34
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 34

Arg Arg Lys Lys Cys Thr Trp Val Arg Phe Ile Asn Cys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 35

Arg Arg Lys Lys Cys Thr Trp Trp Arg Phe Ile Asn Cys
1               5                   10

<210> SEQ ID NO 36
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 36

Arg Arg Lys Lys Cys Thr Trp Tyr Arg Phe Ile Asn Cys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 37

Arg Arg Lys Lys Cys Thr Trp Phe Ala Phe Ile Asn Cys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE

```
<222> LOCATION: (5)..(13)
<223> OTHER INFORMATION: D-amino acids

<400> SEQUENCE: 38

Arg Arg Lys Lys Cys Thr Trp Phe Cys Phe Ile Asn Cys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 39

Arg Arg Lys Lys Cys Thr Trp Phe Asp Phe Ile Asn Cys
1               5                   10

<210> SEQ ID NO 40
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 40

Arg Arg Lys Lys Cys Thr Trp Phe Glu Phe Ile Asn Cys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 41

Arg Arg Lys Lys Cys Thr Trp Phe Phe Phe Ile Asn Cys
1               5                   10

<210> SEQ ID NO 42
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(8)
<223> OTHER INFORMATION: D-amino acids
<220> FEATURE:
<221> NAME/KEY: SITE
<222> LOCATION: (10)..(13)
<223> OTHER INFORMATION: D-amino acids

<400> SEQUENCE: 42

Arg Arg Lys Lys Cys Thr Trp Phe Gly Phe Ile Asn Cys
1               5                   10
```

```
<210> SEQ ID NO 43
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 43

Arg Arg Lys Lys Cys Thr Trp Phe His Phe Ile Asn Cys
1               5                   10

<210> SEQ ID NO 44
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 44

Arg Arg Lys Lys Cys Thr Trp Phe Ile Phe Ile Asn Cys
1               5                   10

<210> SEQ ID NO 45
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 45

Arg Arg Lys Lys Cys Thr Trp Phe Lys Phe Ile Asn Cys
1               5                   10

<210> SEQ ID NO 46
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 46

Arg Arg Lys Lys Cys Thr Trp Phe Leu Phe Ile Asn Cys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
```

```
<223> OTHER INFORMATION: D-amino acids

<400> SEQUENCE: 47

Arg Arg Lys Lys Cys Thr Trp Phe Met Phe Ile Asn Cys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 48

Arg Arg Lys Lys Cys Thr Trp Phe Asn Phe Ile Asn Cys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 49

Arg Arg Lys Lys Cys Thr Trp Phe Pro Phe Ile Asn Cys
1               5                   10

<210> SEQ ID NO 50
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 50

Arg Arg Lys Lys Cys Thr Trp Phe Gln Phe Ile Asn Cys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(12)
<223> OTHER INFORMATION: D-amino acids

<400> SEQUENCE: 51

Arg Arg Lys Lys Cys Trp Trp Phe Thr Trp Ile Ala Cys
1               5                   10

<210> SEQ ID NO 52
<211> LENGTH: 13
<212> TYPE: PRT
```

```
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 52

Arg Arg Lys Lys Cys Thr Trp Phe Ser Phe Ile Asn Cys
1               5                   10

<210> SEQ ID NO 53
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 53

Arg Arg Lys Lys Cys Thr Trp Phe Thr Phe Ile Asn Cys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 54

Arg Arg Lys Lys Cys Thr Trp Phe Val Phe Ile Asn Cys
1               5                   10

<210> SEQ ID NO 55
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 55

Arg Arg Lys Lys Cys Thr Trp Phe Trp Phe Ile Asn Cys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 56

Arg Arg Lys Lys Cys Thr Trp Phe Tyr Phe Ile Asn Cys
```

<210> SEQ ID NO 57
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(12)
<223> OTHER INFORMATION: D-amino acids

<400> SEQUENCE: 57

```
Arg Arg Lys Lys Cys Trp Trp Phe Thr Tyr Ile Ala Cys
1               5                   10
```

<210> SEQ ID NO 58
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 58

```
Arg Arg Lys Lys Cys Ala Trp Phe Thr Phe Ile Asn Cys
1               5                   10
```

<210> SEQ ID NO 59
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 59

```
Arg Arg Lys Lys Cys Cys Trp Phe Thr Phe Ile Asn Cys
1               5                   10
```

<210> SEQ ID NO 60
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 60

```
Arg Arg Lys Lys Cys Asp Trp Phe Thr Phe Ile Asn Cys
1               5                   10
```

<210> SEQ ID NO 61
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE

```
<222> LOCATION: (5)..(13)
<223> OTHER INFORMATION: D-amino acids

<400> SEQUENCE: 61

Arg Arg Lys Lys Cys Glu Trp Phe Thr Phe Ile Asn Cys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 62

Arg Arg Lys Lys Cys Phe Trp Phe Thr Phe Ile Asn Cys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(5)
<223> OTHER INFORMATION: D-amino acids
<220> FEATURE:
<221> NAME/KEY: SITE
<222> LOCATION: (7)..(13)
<223> OTHER INFORMATION: D-amino acids

<400> SEQUENCE: 63

Arg Arg Lys Lys Cys Gly Trp Phe Thr Phe Ile Asn Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 64

Arg Arg Lys Lys Cys His Trp Phe Thr Phe Ile Asn Cys
1               5                   10

<210> SEQ ID NO 65
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 65

Arg Arg Lys Lys Cys Ile Trp Phe Thr Phe Ile Asn Cys
1               5                   10
```

```
<210> SEQ ID NO 66
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 66

Arg Arg Lys Lys Cys Lys Trp Phe Thr Phe Ile Asn Cys
1               5                   10

<210> SEQ ID NO 67
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 67

Arg Arg Lys Lys Cys Leu Trp Phe Thr Phe Ile Asn Cys
1               5                   10

<210> SEQ ID NO 68
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 68

Arg Arg Lys Lys Cys Met Trp Phe Thr Phe Ile Asn Cys
1               5                   10

<210> SEQ ID NO 69
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 69

Arg Arg Lys Lys Cys Asn Trp Phe Thr Phe Ile Asn Cys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
```

<223> OTHER INFORMATION: D-amino acids

<400> SEQUENCE: 70

Arg Arg Lys Lys Cys Pro Trp Phe Thr Phe Ile Asn Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 71

Arg Arg Lys Lys Cys Gln Trp Phe Thr Phe Ile Asn Cys
1               5                   10

<210> SEQ ID NO 72
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 72

Arg Arg Lys Lys Cys Arg Trp Phe Thr Phe Ile Asn Cys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 73

Arg Arg Lys Lys Cys Ser Trp Phe Thr Phe Ile Asn Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 74

Arg Arg Lys Lys Cys Thr Trp Phe Thr Phe Ile Asn Cys
1               5                   10

<210> SEQ ID NO 75
<211> LENGTH: 13
<212> TYPE: PRT

```
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 75

Arg Arg Lys Lys Cys Val Trp Phe Thr Phe Ile Asn Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 76

Arg Arg Lys Lys Cys Trp Trp Phe Thr Phe Ile Asn Cys
1               5                   10

<210> SEQ ID NO 77
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 77

Arg Arg Lys Lys Cys Tyr Trp Phe Thr Phe Ile Asn Cys
1               5                   10

<210> SEQ ID NO 78
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 78

Arg Arg Lys Lys Cys Trp Trp Phe Thr Phe Ile Ala Cys
1               5                   10

<210> SEQ ID NO 79
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 79

Arg Arg Lys Lys Cys Trp Trp Phe Thr Phe Ile Cys Cys
```

```
1               5                   10

<210> SEQ ID NO 80
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 80

Arg Arg Lys Lys Cys Trp Trp Phe Thr Phe Ile Asp Cys
1               5                   10

<210> SEQ ID NO 81
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 81

Arg Arg Lys Lys Cys Trp Trp Phe Thr Phe Ile Glu Cys
1               5                   10

<210> SEQ ID NO 82
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 82

Arg Arg Lys Lys Cys Trp Trp Phe Thr Phe Ile Phe Cys
1               5                   10

<210> SEQ ID NO 83
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(11)
<223> OTHER INFORMATION: D-amino acids
<220> FEATURE:
<221> NAME/KEY: SITE
<222> LOCATION: (13)..(13)
<223> OTHER INFORMATION: D-amino acids

<400> SEQUENCE: 83

Arg Arg Lys Lys Cys Trp Trp Phe Thr Phe Ile Gly Cys
1               5                   10

<210> SEQ ID NO 84
<211> LENGTH: 13
<212> TYPE: PRT
<213> ORGANISM: Artificial Sequence
```

```
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 84

Arg Arg Lys Lys Cys Trp Trp Phe Thr Phe Ile His Cys
1               5                   10

<210> SEQ ID NO 85
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 85

Arg Arg Lys Lys Cys Trp Trp Phe Thr Phe Ile Ile Cys
1               5                   10

<210> SEQ ID NO 86
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 86

Arg Arg Lys Lys Cys Trp Trp Phe Thr Phe Ile Lys Cys
1               5                   10

<210> SEQ ID NO 87
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 87

Arg Arg Lys Lys Cys Trp Trp Phe Thr Phe Ile Leu Cys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 88

Arg Arg Lys Lys Cys Trp Trp Phe Thr Phe Ile Met Cys
1               5                   10
```

<210> SEQ ID NO 89
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 89

Arg Arg Lys Lys Cys Trp Trp Phe Thr Phe Ile Pro Cys
1               5                   10

<210> SEQ ID NO 90
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 90

Arg Arg Lys Lys Cys Trp Trp Phe Thr Phe Ile Gln Cys
1               5                   10

<210> SEQ ID NO 91
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 91

Arg Arg Lys Lys Cys Trp Trp Phe Thr Phe Ile Arg Cys
1               5                   10

<210> SEQ ID NO 92
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 92

Arg Arg Lys Lys Cys Trp Trp Phe Thr Phe Ile Ser Cys
1               5                   10

<210> SEQ ID NO 93
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)

```
<223> OTHER INFORMATION: D-amino acids

<400> SEQUENCE: 93

Arg Arg Lys Lys Cys Trp Trp Phe Thr Phe Ile Thr Cys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 94

Arg Arg Lys Lys Cys Trp Trp Phe Thr Phe Ile Val Cys
1               5                   10

<210> SEQ ID NO 95
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 95

Arg Arg Lys Lys Cys Trp Trp Phe Thr Phe Ile Trp Cys
1               5                   10

<210> SEQ ID NO 96
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(13)
<223> OTHER INFORMATION: D-amino acids

<400> SEQUENCE: 96

Arg Arg Lys Lys Cys Trp Trp Phe Thr Phe Ile Tyr Cys
1               5                   10

<210> SEQ ID NO 97
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 97

Cys Thr Lys Ser Arg Phe Ala Asn Cys
1               5

<210> SEQ ID NO 98
<211> LENGTH: 9
<212> TYPE: PRT
```

```
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 98

Cys Thr Lys Ser Arg Phe Cys Asn Cys
1               5

<210> SEQ ID NO 99
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 99

Cys Thr Lys Ser Arg Phe Glu Asn Cys
1               5

<210> SEQ ID NO 100
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 100

Cys Thr Lys Ser Arg Phe Phe Asn Cys
1               5

<210> SEQ ID NO 101
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(6)
<223> OTHER INFORMATION: D-amino acids
<220> FEATURE:
<221> NAME/KEY: SITE
<222> LOCATION: (8)..(9)
<223> OTHER INFORMATION: D-amino acids

<400> SEQUENCE: 101

Cys Thr Lys Ser Arg Phe Gly Asn Cys
1               5

<210> SEQ ID NO 102
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids
```

```
<400> SEQUENCE: 102

Cys Thr Lys Ser Arg Phe His Asn Cys
1               5

<210> SEQ ID NO 103
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 103

Cys Thr Lys Ser Arg Phe Ile Asn Cys
1               5

<210> SEQ ID NO 104
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 104

Cys Thr Lys Ser Arg Phe Lys Asn Cys
1               5

<210> SEQ ID NO 105
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 105

Cys Thr Lys Ser Arg Phe Leu Asn Cys
1               5

<210> SEQ ID NO 106
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 106

Cys Thr Lys Ser Arg Phe Met Asn Cys
1               5

<210> SEQ ID NO 107
<211> LENGTH: 9
<212> TYPE: PRT
<213> ORGANISM: Artificial Sequence
```

```
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 107

Cys Thr Lys Ser Arg Phe Asn Asn Cys
1               5

<210> SEQ ID NO 108
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 108

Cys Thr Lys Ser Arg Phe Pro Asn Cys
1               5

<210> SEQ ID NO 109
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 109

Cys Thr Lys Ser Arg Phe Gln Asn Cys
1               5

<210> SEQ ID NO 110
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 110

Cys Thr Lys Ser Arg Phe Arg Asn Cys
1               5

<210> SEQ ID NO 111
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 111

Cys Thr Lys Ser Arg Phe Ser Asn Cys
1               5
```

<210> SEQ ID NO 112
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 112

Cys Thr Lys Ser Arg Phe Thr Asn Cys
1               5

<210> SEQ ID NO 113
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 113

Cys Thr Lys Ser Arg Phe Val Asn Cys
1               5

<210> SEQ ID NO 114
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 114

Cys Thr Lys Ser Arg Phe Trp Asn Cys
1               5

<210> SEQ ID NO 115
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(9)
<223> OTHER INFORMATION: D-amino acids

<400> SEQUENCE: 115

Cys Thr Lys Ser Arg Phe Tyr Asn Cys
1               5

<210> SEQ ID NO 116
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)

<223> OTHER INFORMATION: D-amino acids

<400> SEQUENCE: 116

Arg Arg Lys Lys Cys Thr Ala Ser Arg Phe Ile Asn Cys
1               5                   10

<210> SEQ ID NO 117
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 117

Arg Arg Lys Lys Cys Thr Cys Ser Arg Phe Ile Asn Cys
1               5                   10

<210> SEQ ID NO 118
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 118

Arg Arg Lys Lys Cys Thr Asp Ser Arg Phe Ile Asn Cys
1               5                   10

<210> SEQ ID NO 119
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 119

Arg Arg Lys Lys Cys Thr Glu Ser Arg Phe Ile Asn Cys
1               5                   10

<210> SEQ ID NO 120
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 120

Arg Arg Lys Lys Cys Thr Phe Ser Arg Phe Ile Asn Cys
1               5                   10

<210> SEQ ID NO 121
<211> LENGTH: 13
<212> TYPE: PRT

```
<213> ORGANISM: Artificial Sequence
<220> FEATURE:
<223> OTHER INFORMATION: peptide
<220> FEATURE:
<221> NAME/KEY: SITE
<222> LOCATION: (1)..(6)
<223> OTHER INFORMATION: D-amino acids
<220> FEATURE:
<221> NAME/KEY: SITE
<222> LOCATION: (8)..(13)
<223> OTHER INFORMATION: D-amino acids

<400> SEQUENCE: 121

Arg Arg Lys Lys Cys Thr Gly Ser Arg Phe Ile Asn Cys
1               5                   10

<210> SEQ ID NO 122
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 122

Arg Arg Lys Lys Cys Thr His Ser Arg Phe Ile Asn Cys
1               5                   10

<210> SEQ ID NO 123
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 123

Arg Arg Lys Lys Cys Thr Ile Ser Arg Phe Ile Asn Cys
1               5                   10

<210> SEQ ID NO 124
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 124

Arg Arg Lys Lys Cys Thr Lys Ser Arg Phe Ile Asn Cys
1               5                   10

<210> SEQ ID NO 125
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids
```

<400> SEQUENCE: 125

Arg Arg Lys Lys Cys Thr Leu Ser Arg Phe Ile Asn Cys
1               5                   10

<210> SEQ ID NO 126
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 126

Arg Arg Lys Lys Cys Thr Met Ser Arg Phe Ile Asn Cys
1               5                   10

<210> SEQ ID NO 127
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 127

Arg Arg Lys Lys Cys Thr Asn Ser Arg Phe Ile Asn Cys
1               5                   10

<210> SEQ ID NO 128
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 128

Arg Arg Lys Lys Cys Thr Pro Ser Arg Phe Ile Asn Cys
1               5                   10

<210> SEQ ID NO 129
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 129

Arg Arg Lys Lys Cys Thr Gln Ser Arg Phe Ile Asn Cys
1               5                   10

<210> SEQ ID NO 130
<211> LENGTH: 13
<212> TYPE: PRT
<213> ORGANISM: Artificial Sequence

```
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 130

Arg Arg Lys Lys Cys Thr Arg Ser Arg Phe Ile Asn Cys
1               5                   10

<210> SEQ ID NO 131
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 131

Arg Arg Lys Lys Cys Thr Ser Ser Arg Phe Ile Asn Cys
1               5                   10

<210> SEQ ID NO 132
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 132

Arg Arg Lys Lys Cys Thr Thr Ser Arg Phe Ile Asn Cys
1               5                   10

<210> SEQ ID NO 133
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 133

Arg Arg Lys Lys Cys Thr Val Ser Arg Phe Ile Asn Cys
1               5                   10

<210> SEQ ID NO 134
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 134

Arg Arg Lys Lys Cys Thr Trp Ser Arg Phe Ile Asn Cys
1               5                   10
```

<210> SEQ ID NO 135
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 135

Arg Arg Lys Lys Cys Thr Tyr Ser Arg Phe Ile Asn Cys
1               5                   10

<210> SEQ ID NO 136
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 136

Arg Arg Lys Lys Cys Thr Trp Ser Arg Phe Ile Asn Cys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 137

Arg Arg Lys Lys Cys Trp Trp Phe Thr Ala Ile Ala Cys
1               5                   10

<210> SEQ ID NO 138
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 138

Arg Arg Lys Lys Cys Trp Trp Phe Thr Cys Ile Ala Cys
1               5                   10

<210> SEQ ID NO 139
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)

```
<223> OTHER INFORMATION: D-amino acids

<400> SEQUENCE: 139

Arg Arg Lys Lys Cys Trp Trp Phe Thr Asp Ile Ala Cys
1               5                   10

<210> SEQ ID NO 140
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 140

Arg Arg Lys Lys Cys Trp Trp Phe Thr Glu Ile Ala Cys
1               5                   10

<210> SEQ ID NO 141
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 141

Arg Arg Lys Lys Cys Trp Trp Phe Thr Gly Ile Ala Cys
1               5                   10

<210> SEQ ID NO 142
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 142

Arg Arg Lys Lys Cys Trp Trp Phe Thr His Ile Ala Cys
1               5                   10

<210> SEQ ID NO 143
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 143

Arg Arg Lys Lys Cys Trp Trp Phe Thr Ile Ile Ala Cys
1               5                   10

<210> SEQ ID NO 144
<211> LENGTH: 13
<212> TYPE: PRT
```

-continued

```
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 144

Arg Arg Lys Lys Cys Trp Trp Phe Thr Lys Ile Ala Cys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)

<400> SEQUENCE: 145

Arg Arg Lys Lys Cys Trp Trp Phe Thr Leu Ile Ala Cys
1               5                   10

<210> SEQ ID NO 146
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 146

Arg Arg Lys Lys Cys Trp Trp Phe Thr Met Ile Ala Cys
1               5                   10

<210> SEQ ID NO 147
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 147

Arg Arg Lys Lys Cys Trp Trp Phe Thr Asn Ile Ala Cys
1               5                   10

<210> SEQ ID NO 148
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 148

Arg Arg Lys Lys Cys Trp Trp Phe Thr Pro Ile Ala Cys
1               5                   10
```

<210> SEQ ID NO 149
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 149

Arg Arg Lys Lys Cys Trp Trp Phe Thr Gln Ile Ala Cys
1               5                   10

<210> SEQ ID NO 150
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 150

Arg Arg Lys Lys Cys Trp Trp Phe Thr Arg Ile Ala Cys
1               5                   10

<210> SEQ ID NO 151
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 151

Arg Arg Lys Lys Cys Trp Trp Phe Thr Ser Ile Ala Cys
1               5                   10

<210> SEQ ID NO 152
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)
<223> OTHER INFORMATION: D-amino acids

<400> SEQUENCE: 152

Arg Arg Lys Lys Cys Trp Trp Phe Thr Thr Ile Ala Cys
1               5                   10

<210> SEQ ID NO 153
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(13)

```
<223> OTHER INFORMATION: D-amino acids

<400> SEQUENCE: 153

Arg Arg Lys Lys Cys Trp Trp Phe Thr Val Ile Ala Cys
1               5                   10

<210> SEQ ID NO 154
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (1)..(4)
<223> OTHER INFORMATION: D-amino acids
<220> FEATURE:
<221> NAME/KEY: SITE
<222> LOCATION: (5)..(5)
<223> OTHER INFORMATION: any D/L amino acid
<220> FEATURE:
<221> NAME/KEY: SITE
<222> LOCATION: (6)..(7)
<223> OTHER INFORMATION: D-amino acids

<400> SEQUENCE: 154

Trp Trp Phe Thr Xaa Ile Ala
1               5

<210> SEQ ID NO 155
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: SITE
<222> LOCATION: (5)..(9)
<223> OTHER INFORMATION: D-amino acids
<220> FEATURE:
<221> NAME/KEY: SITE
<222> LOCATION: (10)..(10)
<223> OTHER INFORMATION: any D/L amino acid
<220> FEATURE:
<221> NAME/KEY: SITE
<222> LOCATION: (11)..(13)
<223> OTHER INFORMATION: D-amino acids

<400> SEQUENCE: 155

Arg Arg Lys Lys Cys Trp Trp Phe Thr Xaa Ile Ala Cys
1               5                   10

<210> SEQ ID NO 156
<211> LENGTH: 4
<212> TYPE: PRT
<213> ORGANISM: Artificial Sequence
<220> FEATURE:
<223> OTHER INFORMATION: Peptide

<400> SEQUENCE: 156

Arg Arg Lys Lys
1

<210> SEQ ID NO 157
<211> LENGTH: 13
<212> TYPE: PRT
<213> ORGANISM: Artificial Sequence
<220> FEATURE:
<223> OTHER INFORMATION: PEPTIDE

<400> SEQUENCE: 157
```

```
Arg Arg Lys Lys Cys Asn Ile Phe Thr Phe Trp Thr Cys
1               5                   10

<210> SEQ ID NO 158
<211> LENGTH: 9
<212> TYPE: PRT
<213> ORGANISM: Artificial Sequence
<220> FEATURE:
<223> OTHER INFORMATION: PEPTIDE

<400> SEQUENCE: 158

Cys Asn Asp Phe Arg Ser Lys Thr Cys
1               5
```

PEPTIDES AND USES THEREFOR AS ANTIVIRAL AGENTS

CROSS-REFERENCE TO RELATED APPLICATION

This application is a U.S. national entry application under 37 C.F.R. § 371(b) of International Application Serial No. PCT/IB2016/057146 filed Nov. 28, 2016, which claims the right of priority and benefit under 35 U.S.C. §§ 119 & 365 of MY Patent Application No. PI 2015002751 filed on Nov. 27, 2015; and which claims priority under 35 U.S.C. § 119(e) to U.S. Provisional Application Ser. No. 62/335,201, filed May 12, 2016, and to U.S. Provisional Application Ser. No. 62/425,913, filed Nov. 23, 2016, the entirety of the disclosure of each of which is expressly incorporated herein by reference.

TECHNICAL FIELD

This invention relates to therapeutic peptides which possess broad spectrum anti-viral activity against influenza viruses, particularly human influenza viruses.

BACKGROUND

Influenza viruses belong to the family of Orthomyxoviridae which contains viruses with negative sense, single-stranded and segmented RNA genomes. There are five different genera under this family: influenza A, B, C, Thogotovirus and Isavirus. Within the first three genera, influenza A and C infect humans, swine, birds and other mammals, while influenza B almost solely infects humans (Peter Palese, 2007). Influenza viruses are estimated to cause more than 5 million serious cases of illness annually worldwide. The symptoms of influenza infection range from asymptomatic to primary viral pneumonia which can be fatal. The clinical manifestations generally include headache, chills, dry cough, high fever, significant myalgias, malaise and anorexia. The clinical manifestations in children are similar to those in adults except they can exhibit high fever accompanied by febrile convulsions (Peter F Wright, 2007).

Influenza virions are highly pleomorphic and they occur in many shapes including ovoid and long filamentous particles. Structurally, each influenza virion consists of haemagglutinin (HA) (135 Å trimer) and neuraminidase (NA) (60-100 Å trimer) proteins which project prominently on the outer surface of the lipid envelope and present in a 4-5:1 ratio. The inner side of the lipid envelope is lined by the matrix protein, encapsulating a core of negative sense RNAs which consists of 8 segments (7 segments for Influenza C) and are wrapped helically by nucleoprotein. It has been reported that HA and NA play a vital role in viral infection. The HA is responsible for binding to the sialic acid receptors on the membrane of infected cells and viral entry by membrane fusion, whereas the NA is required during the release and spread of progeny virions, following the intracellular viral replication cycle (Peter Palese, 2007).

The RNA genome of influenza viruses can mutate, resulting in "antigenic drift'. In addition, two different subtypes can combine and form a new subtype when they co-infect the same host, also resulting in "antigenic shift". These two types of mutations may cause slight or complete alteration on the surface protein type including its shape, infectious ability and pathogenicity; which eventually render an influenza virus a pandemic or epidemic strain (Peter F Wright, 2007). More than four major pandemics caused by influenza viruses have been reported since the beginning of the last century which resulted in great losses to the international economy and human productivity (Kilbourne, 2006). Recently, a swine origin influenza A (H1N1) virus spread fast around the globe and caused reasonably severe mortality and morbidity among the human population (Echevarria-Zuno et al., 2009). It has been suggested that a highly pathogenic epizootic H5N1 virus would be the next pandemic although it has been reported that it can only spread among bird populations with intermittent human infections at a very high rate for mortality (Webster and Govorkova, 2006). Recently, novel reassortant avian H7N9 viruses were found to be associated with severe and fatal respiratory disease among humans in China (Gao et al., 2013).

Previously, the transmission of avian viruses to humans was not considered as a serious threat. It had been reported that avian viruses do not replicate efficiently in experimentally infected humans (Beare A S, 1991). Consistent with that report, there was no report on serious outbreaks of highly pathogenic avian influenza viruses in humans until 1997 except a very few isolated avian-human transmission cases and they lacked the ability to transmit efficiently from person-to-person. However, recent evidence from person-to-person transmission of H5N1 viruses suggests an increase in the chances of human adapted avian viruses as potential pandemic candidates (Ungchusak et al., 2005; Yang et al., 2007).

Nevertheless, despite the extensive efforts made over the decades around the world to control the infection of influenza viruses, only two classes of anti-influenza virus drugs are currently available for effective treatment. One class acts as an antagonist to the influenza A M2 ion channel protein (amantadine and its derivative rimantadine) (Kolocouris et al., 2007) and the other, which includes oseltamivir, acts in influenza A and B as a neuraminidase inhibitor (Zanamivir, Oseltamivir phosphate & Peramivir) (Kim et al., 1997; von Itzstein et al., 1993; Yun et al., 2008) which binds to the NA protein and makes the virus progeny unable to escape from the host cell and infect other cells. Unfortunately, these anti-viral drugs possess undesirable side effects. Moreover, most of the viral strains have now built resistance to the M2 ion channel blocker and to a lesser extent to the neuraminidase inhibitor, which leads to reduced drug efficacy and increased toxicity (McKimm-Breschkin, 2000; Whitley et al., 2013). It has also been reported that oseltamivir could acerbate the illness and sometimes even cause death (Hama et al., 2011). Various approaches targeting viral RNA transcription (Perez et al., 2010), virus-cell attachment (Jones et al., 2006), prevention of the proteolytic activation of HA (Zhirnov and Klenk, 2011), and prevention of virion budding (Stiver, 2003) have been developed, but so far none of the compounds have been successfully translated into an anti-viral drug for clinical use. Therefore, there is an urgent need to develop novel anti-influenza therapeutics having alternative modes of action.

In recent years, the pharmaceutical companies are facing continuous economic pressure due to the increased cost for R&D, toxicity, lack of efficacy, clinical safety and decreased number of approved new molecular entities. Kola and Landis reported that approximately 90% of these new molecular entities failed during drug development (Kola and Landis, 2004). Therefore, there is an urgent need to obtain alternative approaches to improve pharmaceutical R&D productivity. It is believed herein that peptide-based therapeutics could be one of the best options.

Peptide therapeutics may offer advantages over traditional small molecule based drugs. Firstly, they may offer great efficacy, specificity and selectivity as they often represent an active unit of a protein molecule and thus avoid substantial non-specific binding interactions (Hummel, Reineke, and Reimer, 2006). Secondly, as the degradation products of the peptides are amino acids, the chances of drug-drug interactions should be very much minimized and any toxicity related issues may be avoided (Loffet, 2002). Due to their smaller size than proteins and antibody based therapeutics, peptides can easily penetrate into tissues and organs (Ladner et al., 2004) and are generally less immunogenic (McGregor, 2008). Moreover, their cost of manufacturing can be lower than other bio-therapeutics.

A 9 amino acid peptide (C-P1) from a phage display library (New England Biolabs, USA) has been reported to possess anti-influenza activity in vitro and in ovo. See, for example, Rajik et al "Identification and characterization of a novel antiviral peptide against avian influenza virus H9N2, *Virology Journal*, (2009) 6:74, doi:10.1186/1743-422X-6-74", Rajik et al "A novel peptide inhibits influenza virus replication by preventing the viral attachment to the host cells, *International Journal of Biological Sciences*, 2009; 5(6):543-548", Malaysian patent application No. PI20082061, PCT patent application publication No. WO 2009/151313 A1, European patent No. EP2300492 B1, Japan patent application publication No. JP 2011522561A and U.S. Pat. No. 8,883,480. The peptide C-P1 reportedly inhibits the avian influenza A virus H9N2 replication with modest efficacy. There are however no reports regarding any activity of C-P1 against influenza viruses which infect humans. The precise mechanism of action has not been reported. It has been discovered herein that the activity of C-P1 may be insufficient for practical use, and therefore, there remains an unmet medical need for medicaments capable of preventing and/or treating influenza virus infection.

SUMMARY OF THE INVENTION

It has been surprisingly discovered that peptides comprising the sequence tksrfdn (SEQ ID NO:2), referred to herein as P1-RI-CD, are active against influenza viruses. It has also been surprisingly discovered that peptides comprising sequence variations of P1-RI-CD, where one or more amino acids in P1-RI-CD are replaced with an alternative D-amino acid or L-amino acid, are also highly active against influenza viruses. Peptides described herein (also referred to as Flu Peptide Therapeutics (FPTs)) exhibit antiviral activity that is many-fold better than C-P1, and demonstrate broad spectrum activity against human influenza viruses.

In one illustrative embodiment of invention, peptides with anti-viral properties are described herein. In another embodiment, peptides with anti-influenza properties are described herein. In another illustrative embodiment, peptides that include dextro or a mixture of dextro/levo-amino acids are described herein. In another embodiment, peptides that possess anti-viral properties against multiple types of human influenza viruses along with the types which infect animals and birds and can be used in pharmaceutical compositions for the treatment or prevention of influenza virus infections are described herein.

Additional details regarding FPTs are disclosed in Malaysian Application Serial No. PI2015002751, the entirety of the disclosure of which is incorporated herein by reference.

In another embodiment, the isolated peptide P1-RI-CD is described herein. In another embodiment, analogues and derivatives of P1-RI-CD are described herein. In another embodiment, peptides comprising P1-RI-CD or an analogue or derivative of P1-RI-CD are described herein. In another embodiment, peptides are described herein that do not include the sequence NDFRSKT (SEQ ID NO:1). In another embodiment, peptides are described herein that do not include the sequence CNDFRSKTC (SEQ ID NO:158).

As used herein, the term isolated peptide generally refers to a peptide that is ex-vivo, and/or in bulk form. It is to be understood that isolated peptides can be in admixture with other compounds, and/or in a solution or a suspension.

The sequences of peptides described herein are generally set forth using the conventional single letter code for each amino acid. Codes in uppercase letters correspond to the levo form of an amino acid, and codes in lowercase letters correspond to the dextro form of an amino acid. For example, the single letter code "A" denotes L-alanine, whereas the single letter code "a" denotes D-alanine; "R" denotes L-arginine, whereas "r" denotes D-arginine; and so-forth.

In another embodiment, an isolated peptide comprising the sequence A1-A2-A3-A4-A5-A6-A7, where A1 is t or w, A2 is k or w, A3 is s or f, A4 is r or t, A5 is h, i, n, or w, A6 is i or d, and A7 is n or a, and where any one or two of A1, A2, A3, A4, A5, A6, or A7 is optionally replaced with another D-amino acid or L-amino acid is described herein.

In another embodiment, an isolated peptide comprising the sequence A1-A2-A3-A4-A5-A6-A7, where A1 is t or w, A2 is k or w, A3 is s or f, A4 is r or t, A5 is h, i, n, or w, A6 is i or d, and A7 is n or a, and where any one of A1, A2, A3, A4, A5, A6, or A7 is optionally replaced with another D-amino acid or L-amino acid is described herein.

In another embodiment, an isolated peptide comprising the sequence A1-A2-A3-A4-f-A6-A7, where A1 is t or w, A2 is k or w, A3 is s or f, A4 is r or t, A6 is i or d, and A7 is n or a, and where any one or two of A1, A2, A3, A4, f, A6, or A7 is optionally replaced with another D-amino acid or L-amino acid is described herein.

In another embodiment, an isolated peptide comprising the sequence A1-A2-A3-A4-f-A6-A7, where A1 is t or w, A2 is k or w, A3 is s or f, A4 is r or t, A6 is i or d, and A7 is n or a, and where any one of A1, A2, A3, A4, f, A6, or A7 is optionally replaced with another D-amino acid or L-amino acid is described herein.

In another embodiment, an isolated peptide comprising the sequence A1-A2-A3-A4-f-A6-A7, where A1 is t or w, A2 is k or w, A3 is s or f, A4 is r or t, A6 is i or d, and A7 is n or a, and where any one or two of A1, A2, A3, A4, A6, or A7 is optionally replaced with another D-amino acid or L-amino acid is described herein.

In another embodiment, an isolated peptide comprising the sequence A1-A2-A3-A4-f-A6-A7, where A1 is t or w, A2 is k or w, A3 is s or f, A4 is r or t, A6 is i or d, and A7 is n or a, and where any one of A1, A2, A3, A4, A6, or A7 is optionally replaced with another D-amino acid or L-amino acid is described herein.

In another embodiment, isolated anti-influenza peptides comprising a sequence selected from tksrfX/xn, tX/xsrfin, twX/xrfin, twfX/xfin, X/xwftfin, wwftfiX/x, wwftX/xia, and tksrfdn are described herein.

In another embodiment, a peptide as shown in table 1 with serial number 2-9 or as shown in any of Tables 2-8 are described herein. It is to be understood that functional variants of the peptides in these tables that retain biological activity are also within the scope of the invention described herein.

In another embodiment, peptides which possess antiviral properties against influenza viruses selected from the peptide group consisting of PSP III B1, B2, and B4 to B20, PSP IV A1, A2, A4, A5, and A7 to A20, PSP V A2 to A5, A7 to A11, A14 to A16, and A18 to A20, PSP VI A1 to A8, A10 to A16, and A18 to A20, and PSP VII A1, A7, A8, A10, A12, A13, A15, and A19 are described herein.

In another embodiment, pharmaceutical compositions comprising one or more peptides as described above, for example selected from the group consisting of PSP III B1, B2, and B4 to B20, PSP IV A1, A2, A4, A5, and A7 to A20, PSP V A2 to A5, A7 to A11, A14 to A16, and A18 to A20, PSP VI A1 to A8, A10 to A16, and A18 to A20, and PSP VII A1, A7, A8, A10, A12, A13, A15, and A19 are described herein.

In another embodiment, compositions comprising any of the peptides described herein for treating and/or preventing influenza virus infections in a mammal are described herein.

In another embodiment, methods for treating and/or preventing influenza virus infections in a mammal using any of the peptides described herein and related uses are described herein.

In another embodiment, uses of the peptides described herein with anti-viral properties against influenza for use as a medicament or in the manufacture of a medicament are described herein.

BRIEF DESCRIPTION OF THE DRAWINGS

FIG. 1A: Effect of PSP III B5 and PSP IV A5 against H1N1 in vitro. The ability of PSP III B5 and PSP IV A5 to inhibit the replication of H1N1 A1/Malaysia/302/1954 was determined by Plaque reduction assays on MDCK cells. Experiments were carried out in the presence of DMSO (control) or increasing concentration of PSP III B5 or PSP IV A5. Results are presented as the mean value of triplicate measurements.

FIG. 1B: Effect of PSP III B5 and PSP IV A5 against H3N2 in vitro. The ability of PSP III B5 and PSP IV A5 to inhibit the replication of H3N2 A/HK/8/1968 was determined by Plaque reduction assays on MDCK cells. Experiments were carried out in the presence of DMSO (control) or increasing concentration of PSP III B5 or PSP IV A5. Results are presented as the mean value of triplicate measurements.

FIG. 1C: Effect of PSP III B5 and PSP IV A5 against 2009 pandemic virus in vitro. The ability of PSP III B5 and PSP IV A5 to inhibit the replication of H1N1 A/NY/18/2009 was determined by Plaque reduction assays on MDCK cells. Experiments were carried out in the presence of DMSO (control) or increasing concentration of PSP III B5 or PSP IV A5. Results are presented as the mean value of triplicate measurements.

FIG. 1D: Effect of PSP III B5 and PSP IV A5 against H9N2 in vitro. The ability of PSP III B5 and PSP IV A5 to inhibit the replication of H9N2 A/Iran/16/2000 was determined by Plaque reduction assays on MDCK cells. Experiments were carried out in the presence of DMSO (control) or increasing concentration of PSP III B5 or PSP IV A5. Results are presented as the mean value of triplicate measurements.

FIG. 1E: Effect of PSP III B5 and PSP IV A5 against H3N8 in vitro. The ability of PSP III B5 and PSP IV A5 to inhibit the replication of H3N8 A/Miami/2/63 was determined by Plaque reduction assays on MDCK cells. Experiments were carried out in the presence of DMSO (control) or increasing concentration of PSP III B5 or PSP IV A5. Results are presented as the mean value of triplicate measurements.

FIG. 1F: Effect of PSP III B5 and PSP IV A5 against H5N1 in vitro. The ability of PSP III B5 and PSP IV A5 to inhibit the replication of H5N1 A/Kampung pasir/5744/2004 was determined by Plaque reduction assays on MDCK cells. Experiments were carried out in the presence of DMSO (control) or increasing concentration of PSP III B5 or PSPIVA5. Results are presented as the mean value of triplicate measurements.

FIG. 2: Effect of Oseltamivir acid and PSP IV A5 against H1N1 PR8 in vitro. Comparison of the ability of Oseltamivir acid (comparative example) and PSP IVA5 to inhibit the replication of H1N1 A/PR/8/1934, as determined by Plaque reduction assays on MDCK cells. Experiments were carried out in the presence of DMSO (control) or increasing concentration of Oseltamivir acid or PSP IV A5. Results are presented as the mean value of triplicate measurements.

FIG. 3: Effect of PSP V A19 against H1N1 PR8 in vitro. The ability of PSP V A19 to inhibit the replication of H1N1 A/PR/8/1934 was determined by Plaque reduction assays on MDCK cells. Experiments were carried out in the presence of DMSO (control) or increasing concentration of PSP V A19. Results are presented as the mean value of triplicate measurements.

FIG. 4: Effect of PSP VI A1 against H1N1 PR8 in vitro. The ability of PSP VI A1 to inhibit the replication of H1N1 A/PR/8/1934 was determined by Plaque reduction assays on MDCK cells. Experiments were carried out in the presence of DMSO (control) or increasing concentration of PSP VI A1. Results are presented as the mean value of triplicate measurements.

FIG. 5: Effect of PSP IV A17 against Mouse adapted H1N1 PR8 in vivo. Anti-viral efficacy of FPT in mouse model. Influenza infected mice were treated with 0 mg/kg (control) or 3.5 mg/kg of PSP IV A17 peptide intravenously (qd; 5 days) and the mice were monitored for morbidity and mortality over a period of 14 days. At the end of the observation period, the percentage of survived mice in each group was plotted. Results are representative of at least two different experiments FIG. 6A: Cytotoxic effects of anti-viral peptides in human hepatocytes. Cytotoxic effects of anti-viral peptides (PSP III B3, PSP III B5, PSP III B16, PSP III B19, PSP III B20 and PSP IV A5). Toxicity effects were tested in two different concentrations in human hepatic cell HepaRG™, a cell with a proven differentiated hepatocyte phenotype under the cell-culture conditions. Data are presented as the mean value±standard deviation of triplicate measurements. This experiment was performed as described in Example 5.

FIG. 6B: Cytotoxic effects of anti-viral peptides in human hepatocytes. Cytotoxic effects of anti-viral peptides (PSP IV A17, PSP V A19, PSP V A11, PSP VI A1, and PSP VI A16). Toxicity effects were tested in two different concentrations in human hepatic cell HepaRG™, a cell with a proven differentiated hepatocyte phenotype under the cell-culture conditions. Data are presented as the mean value±standard deviation of triplicate measurements. This experiment was performed as described in Example 5.

FIG. 7A: Cytotoxic effects of anti-viral peptides PSP V A19 on MDCK & A549 cells. Cytotoxic effects of anti-viral peptide PSP V A19. The toxicity effects of the above peptide were tested at many different concentrations on MDCK & A549 cells as described in Example 7. Data are presented as the mean value±standard deviation of triplicate measurements.

FIG. 7B: Cytotoxic effects of anti-viral peptides PSP VI A1 on MDCK & A549 cells. Cytotoxic effects of anti-viral peptide PSP VI A1. The toxicity effects of the above peptide were tested at many different concentrations on MDCK & A549 cells as described in Example 7. Data are presented as the mean value±standard deviation of triplicate measurements.

FIG. 8: Hemolytic activities of different antiviral peptides at 30 μM concentration. Hemolytic activities of Triton X-100 or different antiviral peptides (PSP III B5, PSP IV A17, PSP V A19 & PSP VI A1) were tested at 30 μM concentration as described in Example 8.

FIG. 9: Analysis of peptide treated HIN1 PR8 virus by electron microscopy. The pictures show the electron micrograph of Influenza A H1N1/PR/8 virus treated with either 0, 1 or 100 μM PSP V A19 peptide, at a magnification of 16,000×. The experiment was carried out as described in Example 6; A: No peptide treatment; B: 1 μM peptide treatment; C: 100 μM peptide treatment.

DETAILED DESCRIPTION

The present invention will now be further described by the following illustrative embodiments. In the following passages, different illustrative aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. However, it is to be understood that the invention is not limited to such feature or features indicated as being preferred or advantageous, and any feature or features indicated as being preferred or advantageous are not required.

The practice of the present invention will employ, unless otherwise indicated, conventional techniques of chemistry, biochemistry, molecular biology, recombinant DNA technology, cell biology, immunology and bioinformatics which are within the skill of the art. Such techniques are explained fully in the literature.

Throughout this disclosure, a standard one letter code is used to denote the amino acids in accordance with IUPAC/IUB guidelines. In the sequences listed herein, the left most amino acid at the end of any sequence represents the amino-terminal end (optionally denoted with H—) whereas the right most amino acid represents the carboxy terminal end (optionally denoted with —OH). With the exception of glycine which is achiral, the levo form of amino acids is denoted in uppercase letters herein, and the dextro form of amino acids is denoted in lowercase letters.

The present invention is directed to peptides with anti-influenza activity. In addition, the invention is directed to peptides with anti-influenza activity against more than one influenza virus subtype. In addition, the invention is directed to pharmaceutical compositions comprising peptides described herein, and methods of using peptides described herein to prevent and/or treat influenza viral infections.

Illustrative embodiments of the invention are described by the following clauses:

An isolated peptide of the sequence or comprising the sequence tksrfdn (SEQ ID NO: 2).

An isolated peptide of the sequence or comprising the sequence of a derivative of P1-RI-CD.

An isolated peptide of the sequence or comprising the sequence A1-A2-A3-A4-A5-A6-A7, where A1 is t or w, A2 is k or w, A3 is s or f, A4 is r or t, A5 is h, i, n, or w, A6 is i or d, and A7 is n or a, and where any one or any two of A1, A2, A3, A4, f, A6, or A7 is optionally replaced with another D-amino acid or L-amino acid.

An isolated peptide of the sequence or comprising the sequence A1-A2-A3-A4-A5-A6-A7, where A1 is t or w, A2 is k or w, A3 is s or f, A4 is r or t, A5 is i or w, A6 is i or d, and A7 is n or a, and where any one or any two of A1, A2, A3, A4, f, A6, or A7 is optionally replaced with another D-amino acid or L-amino acid.

The peptide of any one of the preceding clauses where any one of A1, A2, A3, A4, A5, A6, or A7 is optionally replaced with another D-amino acid or L-amino acid.

An isolated peptide of the sequence or comprising the sequence A1-A2-A3-A4-f-A6-A7, where A1 is t or w, A2 is k or w, A3 is s or f, A4 is r or t, A6 is i or d, and A7 is n or a, and where any one or any two of A1, A2, A3, A4, f, A6, or A7 is optionally replaced with another D-amino acid or L-amino acid.

The peptide of the preceding clause where any one of A1, A2, A3, A4, f, A6, or A7 is optionally replaced with another D-amino acid or L-amino acid.

An isolated peptide comprising the sequence A1-A2-A3-A4-f-A6-A7, where A1 is t or w, A2 is k or w, A3 is s or f, A4 is r or t, A6 is i or d, and A7 is n or a, and where any one or any two of A1, A2, A3, A4, A6, or A7 is optionally replaced with another D-amino acid or L-amino acid.

The peptide of the preceding clause where any one of A1, A2, A3, A4, A6, or A7 is optionally replaced with another D-amino acid or L-amino acid.

The peptide of any of the preceding clauses wherein A1 is t.

The peptide of any of the preceding clauses wherein A1-A2 is tk or tw.

The peptide of any of the preceding clauses wherein A2-A3 is ks or wf.

The peptide of any of the preceding clauses wherein A1-A2-A3 is tks or twf.

The peptide of any of the preceding clauses wherein A3-A4 is sr or ft.

The peptide of any of the preceding clauses wherein A2-A3-A4 is ksr or wft.

The peptide of any of the preceding clauses wherein A4 is r or t.

The peptide of any of the preceding clauses wherein A5 is h, i, n, or w.

The peptide of any of the preceding clauses wherein A5 is i or w.

The peptide of any of the preceding clauses wherein A1-A2 is ww.

The peptide of any of the preceding clauses wherein A6-A7 is ia.

The peptide of any of the preceding clauses wherein f is not replaced.

The peptide of any of the preceding clauses wherein A4 is r or t, and A6 is i.

The peptide of any of the preceding clauses wherein A6-A7 is in.

The peptide of any of the preceding clauses wherein A7 is n.

The peptide of any of the preceding clauses comprising tksrfxn, where x is i, l, or y.

The peptide of any of the preceding clauses comprising twf(x2)fin, where (x2) is i, l, m, r, s, t, v, or w.

The peptide of any of the preceding clauses comprising tw(x3)rfin, where (x3) is a, c, e, f, G, h, k, l, m, n, p, q, r, s, t, v, w, or y.

The peptide of any of the preceding clauses comprising t(x4)srfin, where (x4) is p, r, s, or w.

The peptide of any of the preceding clauses comprising (x5)wftfin, where (x5) is m or w.

The peptide of any of the preceding clauses comprising wwft(x6)ia, where (x6) is h, i, n, or w.

The peptide of any of the preceding clauses comprising wwft(x6)ia, where (x6) is i or w.

The peptide of any of the preceding clauses comprising a sequence selected from tksrfX/xn, tX/xsrfin, twX/xrfin, twfX/xfin, X/xwftfin, wwftfiX/x, wwftX/xia, and tksrfdn or a derivative thereof that does not comprise NDFRSKT (SEQ ID NO:1) X/x is glycine or any D-amino acid or L-amino acid.

The peptide of any one of the preceding clauses wherein said peptide has anti-viral activity against an influenza virus A subtype that infects humans.

The peptide of any one of the preceding clauses wherein said peptide has anti-viral activity against more than one influenza virus A subtype that infects humans.

The peptide of any one of the preceding clauses wherein said peptide has anti-viral activity against an influenza virus B subtype that infects humans.

The peptide of any one of the preceding clauses wherein said peptide has anti-viral activity against more than one influenza virus B subtype that infects humans.

The peptide of any one of the preceding clauses further comprising a cysteine residue at the N and C terminus.

The peptide of any one of the preceding clauses further comprising a solubility tag.

The peptide of any one of the preceding clauses wherein said solubility tag is RRKK (SEQ ID NO:156) or rrkk.

The peptide of any one of the preceding clauses selected from ctksrfX/xnc, rrkkctX/xsrfinc, RRKKctwX/xrfinc, RRKKctwfX/xfinc, RRKKcX/xwftfinc, RRKKcwwftfiX/xc, RRKKcwwftX/xiac, and ctksrfdnc.

The peptide of any one of the preceding clauses wherein X/x is selected from any proteinogenic amino acid.

The peptide of any one of the preceding clauses wherein x is selected from a, c, d, e, f, h, k, l, m, n, p, q, r, s, t, v, w, y or G.

The peptide of any one of the preceding clauses which has an IC$_{50}$ of less than 100 μM.

The peptide of any one of the preceding clauses wherein said peptide has the formula RRKKctwX/xrfinc and is selected from RRKKctwarfinc, RRKKctwcrfinc, RRKKctwdrfinc, RRKKctwerfinc, RRKKctwfrfinc, RRKKctwGrfinc, RRKKctwhrfinc, RRKKctwirfinc, RRKKctwkrfinc, RRKKctwlrfinc, RRKKctwmrfinc, RRKKctwnrfinc, RRKKctwprfinc, RRKKctwqrfinc, RRKKctwrrfinc, RRKKctwsrfinc, RRKKctwtrfinc, RRKKctwvrfinc, RRKKctwwrfinc or RRKKctwyrfinc.

The peptide of any one of the preceding clauses wherein said peptide has the formula RRKKctwfX/xfinc and is selected from RRKKctwfafinc, RRKKctwfcfinc, RRKKctwfdfinc, RRKKctwfefinc, RRKKctwfffinc, RRKKctwfGfinc, RRKKctwfhfinc, RRKKctwfifinc, RRKKctwfkfinc, RRKKctwflfinc, RRKKctwfmfinc, RRKKctwfnfinc, RRKKctwfpfinc, RRKKctwfqfinc, RRKKctwfrfinc, RRKKctwfsfinc, RRKKctwftfinc, RRKKctwfvfinc, RRKKctwfwfinc, and RRKKctwfyfinc.

The peptide of any one of the preceding clauses wherein said peptide has the formula RRKKcX/xwftfinc and is selected from RRKKcawftfinc, RRKKccwftfinc, RRKKcdwftfinc, RRKKcewftfinc, RRKKcfwftfinc, RRKKcGwftfinc, RRKKchwftfinc, RRKKciwftfinc, RRKKckwftfinc, RRKKclwftfinc, RRKKcmwftfinc, RRKKcnwftfinc, RRKKcpwftfinc, RRKKcqwftfinc, RRKKcrwftfinc, RRKKcswftfinc, RRKKctwftfinc, RRKKcvwftfinc, RRKKcwwftfinc and RRKKcywftfinc.

The peptide of any one of the preceding clauses wherein said peptide has the formula RRKKcwwftfiX/xc and is selected from RRKKcwwftfiac, RRKKcwwftficc, RRKKcwwftfidc, RRKKcwwftfiec, RRKKcwwftfifc, RRKKcwwftfiGc, RRKKcwwftfihc, RRKKcwwftfiic, RRKKcwwftfikc, RRKKcwwftfilc, RRKKcwwftfimc, RRKKcwwftfipc, RRKKcwwftfiqc, RRKKcwwftfirc, RRKKcwwftfisc, RRKKcwwftfitc, RRKKcwwftfivc, RRKKcwwftfiwc, RRKKcwwftfiyc.

The peptide of any one of the preceding clauses wherein said peptide is selected from ctksrfanc, ctksrfcnc, ctksrfdnc, ctksrfenc, ctksrffnc, ctksrfGnc, ctksrfhnc, ctksrfinc, ctksrfknc, ctksrflnc, ctksrfmnc, ctksrfnnc, ctksrfpnc, ctksrfqnc, ctksrfanc, ctksrfsnc, ctksrftnc, ctksrfvnc, ctksrfwnc and ctksrfync.

The peptide of any one of the preceding clauses wherein said peptide is selected from rrkkctasrfinc, rrkkctcsrfinc, rrkkctdsrfinc, rrkkctesrfinc, rrkkctfsrfinc, rrkkctGsrfinc, rrkkcthsrfinc, rrkkctisrfinc, rrkkctksrfinc, rrkkctlsrfinc, rrkkctmsrfinc, rrkkctnsrfinc, rrkkctpsrfinc, rrkkctqsrfinc, rrkkctrsrfinc, rrkkctssrfinc, rrkkctvsrfinc, rrkkctwsrfinc and rrkkctysrfinc.

The peptide of any one of the preceding clauses wherein said peptide is selected from RRKKcwwftaiac, RRKKcwwftciac, RRKKcwwftdiac, RRKKcwwfteiac, RRKKcwwftGiac, RRKKcwwfthiac, RRKKcwwftiiac, RRKKcwwftkiac, RRKKcwwftliac, RRKKcwwftmiac, RRKKcwwftniac, RRKKcwwftpiac, RRKKcwwftqiac, RRKKcwwftriac, RRKKcwwftsiac, RRKKcwwftviac, RRKKcwwftwiac, and RRKKcwwftyiac.

The peptide of any one of the preceding clauses wherein said peptide is selected from RRKKctwfrfinc, RRKKctwfffinc, RRKKctwftfinc, RRKKcwwftfinc and RRKKcwwftdiac.

The peptide of any one of the preceding clauses wherein said influenza subtype is selected from H2N2, H7N3, H7N7, H7N9, H6N1, H10N8, H1N1, H3N2, H9N2, H3N8 or H5N1.

The peptide of any one of the preceding clauses wherein said influenza subtype is selected from H1N1, H3N2, H9N2, H3N8 or H5N1.

The peptide of any one of the preceding clauses wherein said influenza subtype or strain is selected from a Yamagata lineage and/or a Victoria lineage.

The peptide of any one of the preceding clauses for use as a medicament.

A pharmaceutical composition comprising the peptide of any one of the preceding clauses.

The peptide of any one of the preceding clauses or a pharmaceutical composition thereof adapted for use in the treatment of influenza virus infection.

Use of the peptide of any one of the preceding clauses or a pharmaceutical composition thereof in the manufacture of a medicament for the treatment of influenza virus infection.

A method for treating influenza virus infection in a host animal, the method comprising administering a therapeutically effective amount of the peptide of any one of the preceding clauses or a pharmaceutical composition thereof to the host animal.

The method of any one of the preceding clauses wherein the peptide or pharmaceutical composition is administered by a nasal, pulmonary, intrabronchial, oral or parenteral route.

The method of any one of the preceding clauses wherein the peptide or pharmaceutical composition is administered prophylactically.

The method of any one of the preceding clauses wherein said influenza virus is an influenza A subtype or an influenza B subtype.

The method of any one of the preceding clauses wherein said influenza virus is influenza virus A and the subtype is selected from H1N1, H3N2, H9N2, H3N8 or H5N1.

A method for detecting a peptide that has antiviral activity against influenza comprising making a derivative of the peptide of any one of the preceding clauses and screening for antiviral activity.

A kit comprising the peptide of any one of the preceding clauses or a pharmaceutical composition thereof and instructions for use of the peptide or pharmaceutical composition for treating influenza virus infection.

A vector comprising a nucleic acid encoding the peptide of any one of the preceding clauses.

A plasmid comprising a nucleic acid encoding the peptide of any one of the preceding clauses.

A host cell expressing the peptide of any one of the preceding clauses.

A combination comprising the peptide of any one of the preceding clauses and a second agent selected from a nucleic acid, peptide, protein, contrast agent, antibody, toxin and small molecule.

A recombinant library comprising the peptide of any one of the preceding clauses.

Described herein are novel anti-influenza peptides that include the sequence tksrfdn (SEQ ID NO:2). Also described herein are novel anti-influenza peptides which are based on P1-RI-CD and include N and/or C terminal D-cysteine and/or L-cysteine residues, for cyclization.

Peptides described herein, such as peptide (P1-RI-CD), show greater anti-influenza activity than C-P1. P1-RI-CD is a retro inverso analog of C-P1 where each amino acid is an unnatural D-amino acid, and the sequence is the reverse of C-P1. Moreover, peptides described herein show broad spectrum anti-viral activity against different influenza viruses A subtypes that infect humans.

Without being bound by theory, it is believed herein that the mechanism of action of the FPTs against the influenza viruses derives from the FPTs exerting their action by binding and altering the integrity of the matrix proteins (M1) of the influenza viruses, potentially along with another viral target. As such, peptides described herein are expected to bind and inhibit any matrix containing viruses including, but not limited to, the Retroviridae, lentiviruses, such as HIV; Paramyxoviridae such as paramyxoviruses; Flaviviridae such as flavivirus, hepatitis C virus, tick borne encephalitis, yellow fever and dengue fever viruses; and Filoviridae such as Ebola and Marburg viruses.

Without being bound by theory, it is also believed herein that peptides disclosed herein contain membrane transiting motifs which disrupt the lipid envelopes of the influenza viruses in order to gain access to the underlying matrix proteins which may play a crucial role in their anti-viral activity. Hence the peptides of the present invention are expected to bind and inhibit any lipid envelope containing viruses including, but not limited to, the Togaviridae including rubella virus; the Retroviridae, including lentiviruses, such as HIV; Bunyaviridae such as hantaviruses and arenaviruses; Herpesviridae such as herpes viruses and cytomegaloviruses; Hepnaviridae such as hepatitis B viruses; Paramyxoviridae such as paramyxoviruses; Flaviviridae such as flavivirus, hepatitis C virus, tick borne encephalitis, yellow fever and dengue fever viruses; Filoviridae such as Ebola and Marburg viruses; and Coronaviridae such as coronaviruses including SARS virus and toroviruses.

P1-RI-CD was used as a basis for designing derivatives by applying a positional scanning strategy where original amino acids within the sequence of P1-RI-CD were replaced by an alternative amino acid, such as one of the naturally occurring amino acids, or an alternative D-amino acid, one or more at a time, and checked for their activity in vitro. The highly active peptide from the PSP library was selected for subsequent modifications using the same method. Illustrative libraries, PSP II, III, IV, V, VI, and VII, are shown in Table 1.

The positional scanning yielded additional anti-viral peptides with nanomolar $IC_{50}$ values (Table 10). The activities of these peptides are improved compared to that of the C-P1 peptide. For example, peptides in the PSP VIA family have extremely high potency (>30000 times better than C-P1) against the avian influenza viruses tested. In particular, whilst C-P1 demonstrated activity only against avian influenza virus, the peptides of the invention are active against a wide variety of influenza viruses including the viruses that infect humans.

Derivatives of P1-RI-CD include peptides wherein one or more amino acids are deleted or substituted with a different amino acid as shown in table 1. Derivatives also include peptides with at least 80%, 85%, 90% or 95% sequence identity. Derivatives preferably comprise, consist essentially of, or consist of 7 amino acids. In another embodiment, the derivative comprises a core peptide of 7 amino acids and further comprises additional amino acids to improve various properties, solubility or enable cyclization as described herein. The core peptide is the active peptide, that is the peptide that confers antiviral activity. Derivatives are functional, that is they are biologically active and demonstrate antiviral properties against influenza virus, preferably against more than one influenza virus A subtype that infects humans.

The term "peptide" as used herein refers to a polymer that includes amino acid residues. In illustrative embodiments, the peptide includes from 2 to about 100 residues or 2 to about 50 residues. In other embodiments, the peptide includes about 7 to 20 residues, for example 7 to 10, 11, 12, 13, 14, 15, 16, 17, 18 or 19 residues. In certain embodiments, the amino acid residues comprising the peptide are all "D-form" amino acid residues, however, it is recognized that in various embodiments, "L" amino acids can be incorporated into the peptide. Thus, in some embodiments, the peptides of the invention are a mixture of D-form and L-form amino acids. For example, the peptide may comprise a core of 7 D-amino acids wherein one or more amino acids may be in the L form.

Peptides also include amino acid polymers in which one or more amino acid residues is an artificial chemical analogue of a corresponding naturally occurring amino acid, or the D-amino acid analogue, as well as naturally occurring amino acid polymers. In addition, the term applies to amino acids joined by a peptide linkage or by other, "modified linkages" (e.g. where the peptide bond is replaced by an α-ester, a β-ester, a thioamide, phosphonamide, carbamate, hydroxylate, and the like).

In certain embodiments, peptides of the invention comprise an active core peptide with 7 residues. Additionally, the peptide may comprise further residues, including but not limited to one or more residues that may allow the peptide to form a cyclic peptide and/or one or more residues that increase solubility of the peptide as described herein.

Peptides described herein can be naturally occurring or not naturally occurring. They can be a) produced by chemical synthesis, b) produced by recombinant DNA technology, c) produced by biochemical or enzymatic fragmentation of larger molecules, d) produced by combination of any of the methods listed above from a to d, e) produced by any other means for producing peptides. In another embodiment, the peptide is not naturally occurring. In another embodiment, the peptide comprises a modification that is not naturally occurring. Examples of such modifications are described herein.

TABLE 1

Illustrative families of P1-RI-CD derivatives; the N and C terminus is shown for clarification.

| Serial No. | Group ID | Core Sequence | Sequence of illustrative cyclized peptides and cyclized peptides with a solubility tag |
|---|---|---|---|
| 1 | C-P1 (P1-C) (comparative example) | NDFRSKT SEQ ID NO: 1 | H-CNDFRSKTC-OH SEQ ID NO: 3 |
| 2 | P1-RI-CD | tksrfdn SEQ ID NO: 2 | H-ctksrfdnc-OH SEQ ID NO: 4 |
| 3 | PSP | tksrfX/xn Formula I SEQ ID NO: 5 | H-ctksrfX/xnc-OH SEQ ID NO: 6 |
| 4 | PSP II A | tX/xsrfin Formula II SEQ ID NO: 7 | H-rrkkctX/xsrfinc-OH SEQ ID NO: 8 |
| 5 | PSP III B | twX/xrfin Formula V SEQ ID NO: 9 | H-RRKKctwX/xrfinc-OH SEQ ID NO: 10 |
| 6 | PSP IV A | twfX/xfin Formula VI SEQ ID NO: 11 | H-RRKKctwfX/xfinc-OH SEQ ID NO: 12 |
| 7 | PSP V A | X/xwftfin Formula VII SEQ ID NO: 13 | H-RRKKcX/xwftfinc-OH SEQ ID NO: 14 |
| 8 | PSP VI A | wwftfiX/x Formula VIII SEQ ID NO: 15 | H-RRKKcwwftfiX/xc-OH SEQ ID NO: 16 |
| 9 | PSP VII A | wwftX/xia Formula IX SEQ ID NO: 154 | H-RRKKcwwftX/xiac-OH SEQ ID NO: 155 |

In another embodiment, an anti-influenza peptide comprising, consisting essentially of, or consisting of a sequence selected from tksrfX/xn, tX/xsrfin, twX/xrfin, twfX/xfin, X/xwftfin, wwftfiX/x, wwftX/xia, and tksrfdn (SEQ ID NO:2) is described. In another embodiment, an anti-influenza peptide comprising, consisting essentially of, or consisting of a sequence selected from tksrfX/xn, tX/xsrfin, twX/xrfin, twfX/xfin, X/xwftfin, wwftfiX/x, and wwftX/xia is described.

In another embodiment, an anti-influenza peptide comprising, consisting essentially of, or consisting of a sequence selected from ctksrfX/xnc, ctX/xsrfinc, ctwX/xrfinc, ctwfX/xfinc, cX/xwftfinc, cwwftfiX/xc, cwwftX/xiac, and ctksrfdnc is described. In another embodiment, an anti-influenza peptide comprising, consisting essentially of, or consisting of a sequence selected from ctksrfX/xnc, ctX/xsrfinc, ctwX/xrfinc, ctwfX/xfinc, cX/xwftfinc, cwwftfiX/xc, and cwwftX/xiac is described.

In another embodiment, an anti-influenza peptide comprising, consisting essentially of, or consisting of a sequence selected from RRKKctksrfX/xnc, RRKKctX/xsrfinc, RRKKctwX/xrfinc, RRKKctwfX/xfinc, RRKKcX/xwftfinc, RRKKcwwftfiX/xc, RRKKcwwftX/xiac, and RRKKctksrfdnc is described. In another embodiment, an anti-influenza peptide comprising, consisting essentially of, or consisting of a sequence selected from RRKKctksrfX/xnc, RRKKctX/xsrfinc, RRKKctwX/xrfinc, RRKKctwfX/xfinc, RRKKcX/xwftfinc, RRKKcwwftfiX/xc, and RRKKcwwftX/xiac is described.

In another embodiment, an anti-influenza peptide comprising, consisting essentially of, or consisting of a sequence selected from rrkkctksrfX/xnc, rrkkctX/xsrfinc, rrkkctwX/xrfinc, rrkkctwfX/xfinc, rrkkcX/xwftfinc, rrkkcwwftfiX/xc, rrkkcwwftX/xiac, and rrkkctksrfdnc is described. In another embodiment, an anti-influenza peptide comprising, consisting essentially of, or consisting of a sequence selected from rrkkctksrfX/xnc, rrkkctX/xsrfinc, rrkkctwX/xrfinc, rrkkawfX/xfinc, rrkkcX/xwftfinc, rrkkcwwftfiX/xc, and rrkkcwwftX/xiac is described.

It is to be understood that in any of the foregoing embodiments, the D-cysteine can be L-cysteine.

In the sequences described herein, the amino acid designation "X/x" represents the position where a substitution is made, which may include any L-amino acid or D-amino acid, or any amino acid analogue. The letter "X/x" denotes any proteinogenic amino acid, that is any one of 20 naturally occurring amino acids. With the exception of G which is achiral, X denotes an amino acid in the L form and x denotes an amino acid in the D form.

In another embodiment, X/x is x, that is an amino acid in the D form, or X, that is an amino acid in the L form. In another embodiment, x is selected from the following amino acids in the D form: a, c, d, e, f, h, i, k, l, m, n, p, q, r, s, t, v, w, or y. In another embodiment, X is selected from the following amino acids in the L form: A, C, D, E, F, H, I, K, L, M, N, P, Q, R, S, T, V, W or Y. In another embodiment, X is glycine.

In another embodiment, the peptide has an $IC_{50}$ of less than 100 µM, or less than 50 µM, or less than 10 µM, or less than 5 µM, or less than 1 µM, or less than 0.1 µM. In another embodiment, the peptide shows at least 10%, 20%, 30%, 40%, 50%, 60%, 70%, 80%, 90%, 95% or more inhibition of at least one influenza virus and/or at least one influenza virus subtype, preferably of at least two influenza viruses and/or at least two influenza virus subtypes. Preferably, inhibition is at least 50%, 60%, 70%, 80%, 90%, 95% or more, or at least 75%, 80%, 90%, 95% or more.

In another embodiment, the peptide has antiviral activity against preferably 2, 3, 4 or more influenza virus A subtypes as measured using, for example, 0.01 µM to 100 µM of a peptide in a plaque reduction assay on MDCK cells. In another embodiment, the peptide shows at least 75%, 80%, 90% or 95% inhibition of at least two influenza virus A subtypes.

In another embodiment, the peptide of the invention comprises one or more solubility tags. In one illustrative embodiment, a solubility tag is a short peptide made up of charged amino acids, that, when covalently attached to N-terminal or C-terminal end of a hydrophobic peptide, will increase the solubility of the linked peptide. For example, the solubility tag may comprise one or more amino acid selected from D, E, H, K, N, Q, R, S, T, hydroxy-proline and pyro-glutamic acid as these possess hydrophilic characters. These can be either in levo or dextro form. Adding any of these amino-acids in any combination or repetition, either at N terminal or C terminal end, especially E/D/R/K, can be used to increase the solubility of a peptide. Solubility can also be increased by adding the dipeptide EE, the tripeptide SGS and/or with Hyperglycosylation and PEGylation or other methods known in the art for increasing solubility.

For example, the solubility tag may comprise or consist of solubility tag RRKK (SEQ ID NO:156) (either in levo form RRKK (SEQ ID NO:156) or dextro form rrkk) attached to the N and/or C terminal end of the peptide.

The peptide of the invention may be in linear or in cyclic form. In another embodiment, the peptide of the invention is in cyclic form. The peptides can be cyclized, for example, by formation of a disulfide bond between cysteine residues (or, more generally, between two of the at least two cysteine residues present in the polypeptide (e.g., at the terminal regions)). It is to be understood that each cysteine residue is independently D-cysteine or L-cysteine. For example, one can add at least two cysteine residues, one or both of which are, optionally, at the C-terminal or N-terminal of the peptide. Thus, the anti-viral peptides as well as their derivatives may be cyclized by disulfide bond with their terminal cysteine residues. As shown herein, linear versions of the peptides (i.e. without any cyclization) show anti-viral properties. It is also to be understood that where a peptide contains three or more cysteine residues, one or more of the residues may be modified in order to prevent that residue from participating in formation of a disulfide bond. Conveniently this may be achieved by protecting the thiol group of the cysteine with acetamidomethyl, to form the cysteine analogue acetamidomethyl-cysteine (Cys(Acm)). In the context of the peptides of the present invention, this may be done with the internal cysteine residues of SEQ ID NOs: 18, 38, 59, 79, 98, and 117. Modification can be carried out during synthesis (i.e., the modified residue is used for synthesis), or may be carried out post-synthesis.

Strategies for the preparation of cyclic polypeptides from linear precursors have been described and can be employed with the present peptides. For example, approaches include chemical cross-linking, chemical intramolecular ligation methods and enzymatic intramolecular ligation methods, which allow linear synthetic peptides to be efficiently cyclized under aqueous conditions.

In another embodiment, peptides in cyclic form and comprising a solubility tag, for example RRKK (either in levo or dextro form) are described herein.

In another embodiment, the peptide is selected from ctksrfX/xnc, rrkkctX/xsrfinc, RRKKctwX/xrfinc, RRKctwfX/xfinc, RRKKcX/wftfinc or RRKKcwwftfiX/xc, RRKKcwwftX/xiac, or ctksrfdnc.

In another embodiment, the peptide of the invention has the general formula twX/xrfin (formula V), where X/x is a, c, d, e, f, l, m, n, p, q, r, s, t, v, w, or y. The peptide may comprise a cysteine residue at the N and C terminal end for cyclisation and/or a solubility tag. In another embodiment, the peptide is selected from RRKKctwarfinc, RRKKctwcrfinc, RRKKctwdrfinc, RRKKctwerfinc, RRKKctwfrfinc, RRKKctwGrfinc, RRKKctwhrfinc, RRKKctwirfinc, RRKKctwkrfinc, RRKKctwlrfinc, RRKKctwmrfinc, RRKKctwnrfinc, RRKKctwprfinc, RRKKctwqrfinc, RRKKctwrrfinc, RRKKctwsrfinc, RRKKctwtrfinc, RRKKctwvrfinc, RRKKctwwrfinc or RRKKctwyrfinc. Activities for these peptides against different influenza viruses are shown in Table 2. Also within the scope of the invention are peptides as shown above wherein the solubility tag is in the D form (rrkk). Also within the scope of the invention are functional derivatives of these peptides which are without any cyclization.

TABLE 2

50 µM of each peptide was screened for their anti-viral activity against various influenza viruses via plaque reduction assay on MDCK cells. Data are presented as the mean value of triplicate measurements.

| FPT ID | Sequence | % inhibition | | | |
|---|---|---|---|---|---|
| | | H9N2 | H1N1 | H3N8 | H3N2 |
| PSP III B1 | H-RRKKctwarfinc-OH SEQ ID NO: 17 | 95% | 85% | 96% | 92% |
| PSP III B2 | H-RRKKctwcrfinc-OH SEQ ID NO: 18 | 74% | 71% | 87% | 96% |
| PSP III B3 | H-RRKKctwdrfinc-OH SEQ ID NO: 19 | 20% | 12% | 43% | 83% |
| PSP III B4 | H-RRKKctwerfinc-OH SEQ ID NO: 20 | 86% | 81% | 91% | 100% |
| PSP III B5 | H-RRKKctwfrfinc-OH SEQ ID NO: 21 | 90% | 96% | 100% | 100% |
| PSP III B6 | H-RRKKctwGrfinc-OH SEQ ID NO: 22 | 93% | 85% | 96% | 100% |
| PSP III B7 | H-RRKKctwGrfinc-OH SEQ ID NO: 23 | 88% | 83% | 87% | 96% |
| PSP III B8 | H-RRKKctwirfinc-OH SEQ ID NO: 24 | 81% | 88% | 91% | 100% |
| PSP III B9 | H-RRKKctwkrfinc-OH SEQ ID NO: 25 | 90% | 90% | 96% | 96% |
| PSP III B10 | H-RRKKctwlrfinc-OH SEQ ID NO: 26 | 90% | 92% | 96% | 100% |
| PSP III B11 | H-RRKKctwmrfinc-OH SEQ ID NO:27 | 93% | 94% | 96% | 100% |
| PSP III B12 | H-RRKKctwnrfinc-OH SEQ ID NO: 28 | 83% | 75% | 87% | 100% |
| PSP III B13 | H-RRKKctwprfinc-OH SEQ ID NO: 29 | 79% | 63% | 83% | 96% |
| PSP III B14 | H-RRKKctwqrfinc-OH SEQ ID NO: 30 | 86% | 83% | 87% | 96% |
| PSP III B15 | H-RRKKctwrrfinc-OH SEQ ID NO: 31 | 84% | 83% | 91% | 100% |
| PSP III B16 | H-RRKKctwsrfinc-OH SEQ ID NO: 32 | 88% | 88% | 96% | 96% |
| PSP III B17 | H-RRKKctwtrfinc-OH SEQ ID NO: 33 | 86% | 79% | 96% | 96% |
| PSP III B18 | H-RRKKctwvrfinc-OH SEQ ID NO: 34 | 88% | 90% | 100% | 100% |
| PSP III B19 | H-RRKKctwwrfinc-OH SEQ ID NO: 35 | 97% | 94% | 100% | 100% |
| PSP III B20 | H-RRKKctwyrfinc-OH SEQ ID NO: 36 | 86% | 83% | 96% | 100% |

In another embodiment, the peptide of the invention has the general formula twfX/xfin (formula VI), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from RRKKctwfafinc, RRKKctwfcfinc, RRKKctwfdfinc, RRKKctwfefinc, RRKKctwfffinc, RRKKctwfGfinc, RRKKctwfhfinc, RRKKctwfifinc, RRKKctwfkfinc, RRKKctwflfinc, RRKKctwfmfinc, RRKKctwfnfinc, RRKKctwfpfinc, RRKKctwfqfinc, RRKKctwfrfinc, RRKKctwfsfinc, RRKKctwftfinc, RRKKctwfvfinc, RRKKctwfwfinc, and RRKKctwfyfinc. Activities for these peptides against different influenza viruses are shown in Table 3. Also within the scope of the invention are peptides as shown above wherein the solubility tag is in the D form (rrkk). Also within the scope of the invention are functional derivatives of these peptides which are without any cyclization.

TABLE 3

10 µM of each peptide was screened for their anti-viral activity against various influenza viruses by plaque reduction assay on MDCK cells. Data are presented as the mean value of triplicate measurements.

| | | % Inhibition | | | | | |
|---|---|---|---|---|---|---|---|
| FPT ID | Sequence | H9N2 | H1N1 | H3N8 | H3N2 | Pdm 2009 | PR/8 |
| PSP IV A1 | H-RRKKctwfafinc-OH SEQ ID NO: 37 | 77% | 78% | 83% | — | 78% | — |
| PSP IV A2 | H-RRKKctwfcfinc-OH SEQ ID NO: 38 | 64% | 60% | 76% | 82% | 68% | 68% |
| PSP IV A3 | H-RRKKctwfdfinc-OH SEQ ID NO: 39 | 30% | 49% | 59% | — | 72% | — |
| PSP IV A4 | H-RRKKctwfefinc-OH SEQ ID NO: 40 | 53% | 62% | 72% | — | 45% | — |
| PSP IV A5 | H-RRKKctwfffinc-OH SEQ ID NO: 41 | 93% | 99% | 98% | 99% | 98% | 99% |
| PSP IV A6 | H-RRKKctwfGfinc-OH SEQ ID NO: 42 | 35% | 59% | 57% | — | 47% | — |
| PSP IV A7 | H-RRKKctwfhfinc-OH SEQ ID NO: 43 | 65% | 68% | 79% | 80% | 71% | 73% |
| PSP IV A8 | H-RRKKctwfifinc-OH SEQ ID NO: 44 | 92% | 92% | 96% | 96% | 95% | 97% |
| PSP IV A9 | H-RRKKctwfkfinc-OH SEQ ID NO: 45 | 39% | 56% | 79% | 73% | 66% | 74% |
| PSP IV A10 | H-RRKKctwflfinc-OH SEQ ID NO: 46 | 97% | 90% | 96% | 96% | 85% | 96% |
| PSP IV A11 | H-RRKKctwfmfinc-OH SEQ ID NO: 47 | 84% | 89% | 93% | 90% | 88% | 85% |
| PSP IV A12 | H-RRKKctwfnfinc-OH SEQ ID NO: 48 | 48% | 67% | 56% | | 60% | |
| PSP IV A13 | H-RRKKctwfpfinc-OH SEQ ID NO: 49 | 55% | 52% | 69% | 74% | 65% | 66% |
| PSP IV A14 | H-RRKKctwfqfinc-OH SEQ ID NO: 50 | 68% | 66% | 83% | 83% | 74% | 77% |
| PSP IV A15 | H-RRKKctwfrfinc-OH SEQ ID NO: 21 | 76% | 80% | 92% | 87% | 73% | 88% |
| PSP IV A16 | H-RRKKctwfsfinc-OH SEQ ID NO: 52 | 89% | 91% | 93% | 96% | 81% | 78% |
| PSP IV A17 | H-RRKKctwftfinc-OH SEQ ID NO: 53 | 92% | 91% | 97% | 97% | 97% | 97% |
| PSP IV A18 | H-RRKKctwfvfinc-OH SEQ ID NO: 54 | 95% | 84% | 96% | 96% | 97% | 96% |
| PSP IV A19 | H-RRKKctwfwfinc-OH SEQ ID NO: 55 | 95% | 87% | 94% | 94% | 94% | 90% |

TABLE 3-continued

10 μM of each peptide was screened for their anti-viral activity against various influenza viruses by plaque reduction assay on MDCK cells. Data are presented as the mean value of triplicate measurements.

| | | % Inhibition | | | | | |
|---|---|---|---|---|---|---|---|
| FPT ID | Sequence | H9N2 | H1N1 | H3N8 | H3N2 | Pdm 2009 | PR/8 |
| PSP IV A20 | H-RRKKctwfyfinc-OH SEQ ID NO: 56 | 85% | 79% | 89% | 89% | 79% | 85% |

In another embodiment, the peptide of the invention has the general formula X/xwftfin (formula VII), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from RRKKcawftfinc, RRKKccwftfinc, RRKKcdwftfinc, RRKKcewftfinc, RRKKcfwftfinc, RRKKcGwftfinc, RRKKchwftfinc, RRKKciwftfinc, RRKKckwftfinc, RRKKclwftfinc, RRKKcmwftfinc, RRKKcnwftfinc, RRKKcpwftfinc, RRKKcqwftfinc, RRKKcrwftfinc, RRKKcswftfinc, RRKKctwftfinc, RRKKcvwftfinc, RRKKcwwftfinc and RRKKcywftfinc. Activities for these peptides against different influenza viruses are shown in Table 4. Also within the scope of the invention are peptides as shown above wherein the solubility tag is in the D form (rrkk). Also within the scope of the invention are functional derivatives of these peptides which are without any cyclization.

TABLE 4

1 μM of each peptide was screened for their anti-viral activity against various influenza virus H1N1 A/PR/8/34 by plaque reduction assay on MDCK cells. Data are presented as the mean value of triplicate measurements.

| FPT ID | Sequence | % Inhibition |
|---|---|---|
| PSP V A1 | H-RRKKcawftfinc-OH SEQ ID NO: 58 | <20% |
| PSP V A2 | H-RRKKccwftfinc-OH SEQ ID NO: 59 | <20% |
| PSP V A3 | H-RRKKcdwftfinc-OH SEQ ID NO: 60 | <20% |
| PSP V A4 | H-RRKKcewftfinc-OH SEQ ID NO: 61 | 27% |
| PSP V A5 | H-RRKKcfWftfinc-OH SEQ ID NO: 62 | 57% |
| PSP V A6 | H-RRKKcGwftfinc-OH SEQ ID NO: 63 | <20% |
| PSP V A7 | H-RRKKchwitfinc-OH SEQ ID NO: 64 | 67% |
| PSP V A8 | H-RRKKciwftfinc-OH SEQ ID NO:65 | 20% |
| PSP V A9 | H-RRKKckwftfinc-OH SEQ ID NO: 66 | 77% |
| PSP V A10 | H-RRKKclwftfinc-OH SEQ ID NO: 67 | 65% |
| PSP V A11 | M-RRKKcmwftfinc-OH SEQ ID NO: 68 | 92% |
| PSP V A12 | H-RRKKcnwftfinc-OH SEQ ID NO: 69 | <20% |
| PSP V A13 | H-RRKKcpwftfinc-OH SEQ ID NO: 70 | <20% |
| PSP V A14 | H-RRKKcqwftfinc-OH SEQ ID NO: 71 | 44% |
| PSP V A15 | H-RRKKcrwftfinc-OH SEQ ID NO: 72 | 87% |
| PSP V A16 | H-RRKKcswftfinc-OH SEQ ID NO: 73 | 54% |
| PSP V A17 | H-RRKKctwftfinc-OH SEQ ID NO: 74 | <20% |
| PSP V A18 | H-RRKKcvwftfinc-OH SEQ ID NO: 75 | 81% |
| PSP V A19 | H-RRKKcwwftfinc-OH SEQ ID NO: 76 | 97% |
| PSP V A20 | H-RRKKcywftfinc-OH SEQ ID NO: 77 | <20% |

In another embodiment, the peptide of the invention has the general formula wwftfiX/x (formula VIII), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from RRKKcwwftfiac, RRKKcwwftficc, RRKKcwwftfidc, RRKKcwwftfiec, RRKKcwwftfifc, RRKKcwwftfiGc, RRKKcwwftfihc, RRKKcwwftfiic, RRKKcwwftfikc, RRKKcwwftfilc, RRKKcwwftfimc, RRKKcwwftfipc, RRKKcwwftfiqc, RRKKcwwftfirc, RRKKcwwftfisc, RRKKcwwftfitc, RRKKcwwftfivc, RRKKcwwftfiwc, RRKKcwwftfiyc. Activities for these peptides against different influenza viruses are shown in Table 5. Also within the scope of the invention are peptides as shown above wherein the solubility tag is in the D form (rrkk). Also within the scope of the invention are functional derivatives of these peptides which are without any cyclization.

TABLE 5

1 µM of each peptide from PSP VI A library was screened for their anti-viral activity against various influenza virus H1N1 A/PR/8/34 by plaque reduction assay on MDCK cells. Data are presented as the mean value of triplicate measurements.

| Peptide ID | Sequence | % Inhibition |
|---|---|---|
| PSP VI A1 | H-RRKKcwwftfiac-OH SEQ ID NO: 78 | 98.5 |
| PSP VI A2 | H-RRKKcwwftficc-OH SEQ ID NO: 79 | 95 |
| PSP VI A3 | H-RRKKcwwftfidc-OH SEQ ID NO: 80 | 66 |
| PSP VI A4 | H-RRKKcwwftfiec-OH SEQ ID NO: 81 | 65 |
| PSP VI A5 | H-RRKKcwwftfifc-OH SEQ ID NO: 82 | 60 |
| PSP VI A6 | H RRKKcwwftfiGc-OH SEQ ID NO: 83 | 69 |
| PSP VI A7 | H-RRKKcwwftfihc-OH SEQ ID NO: 84 | 38.5 |
| PSP VI A8 | H-RRKKcwwftfiic-OH SEQ ID NO: 85 | 49 |
| PSP VI A9 | H-RRKKcwwftfikc-OH SEQ ID NO: 86 | 11 |
| PSP VI A10 | H-RRKKcwwftfilc-OH SEQ ID NO: 87 | 48 |
| PSP VI A11 | H-RRKKcwwftfimc-OH SEQ ID NO: 88 | 79 |
| PSP VI A13 | H-RRKKcwwftfipc-OH SEQ ID NO: 89 | 42 |
| PSP VI A14 | H-RRKKcwwftfiqc-OH SEQ ID NO: 90 | 85 |
| PSP VI A15 | H-RRKKcwwftfirc-OH SEQ ID NO: 91 | 92 |
| PSP VI A16 | H-RRKKcwwftfisc-OH SEQ ID NO: 92 | 74 |
| PSP VI A17 | H-RRKKcwwftfitc-OH SEQ ID NO: 93 | 27 |
| PSP VI A18 | H-RRKKcwwftfivc-OH SEQ ID NO: 94 | 53 |
| PSP VI A19 | H-RRKKcwwftfiwc-OH SEQ ID NO: 95 | 78 |
| PSP VI A20 | H-RRKKcwwftfiyc-OH SEQ ID NO: 96 | 53 |

In another embodiment, the peptide of the invention has the general formula tksrfX/xn (formula I), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from ctksrfanc, ctksrfcnc, ctksrfdnc, ctksrfenc, ctksrffnc, ctksrfGnc, ctksrfhnc, ctksrftnc, ctksrfknc, ctksrflnc, ctksrfmnc, ctksrfnnc, ctksrfpnc, ctksrfqnc, ctksrfrnc, ctksrfsnc, ctksrflnc, ctksrfvnc, ctksrfwnc and ctksrfync. Activities for these peptides against different influenza viruses are shown in Table 6. Also within the scope of the invention are peptides as shown above wherein the solubility tag is in the L form (RRKK) (SEQ ID NO:156) or D form (rrkk). Also within the scope of the invention are functional derivatives of these peptides which are without any cyclization.

TABLE 6

500 µM of each peptide was screened for their anti-viral activity against various influenza viruses by plaque reduction assay on MDCK cells. Data are presented as the mean value of duplicate or triplicate measurements.

| 500 µM | | % inhibition | | | |
|---|---|---|---|---|---|
| FPT ID | Sequence | H9N2 | H1N1 | H3N8 | H3N2 |
| PSP 1 | H-ctksrfanc-OH SEQ ID NO: 97 | 36.4 | 29.4 | 79.4 | 70.4 |
| PSP 2 | H-ctksrfcnc-OH SEQ ID NO: 98 | NA | 67.6 | 65 | 18.5 |
| PSP 3 (P1-RI-CD) | H-ctksrfdnc-OH SEQ ID NO: 4 | >50 | 29.4 | 67 | 74.1 |
| PSP 4 | H-ctksrfenc-OH SEQ ID NO: 99 | ND | 52.9 | 64 | 22.7 |
| PSP 5 | H-ctksrffnc-OH SEQ ID NO: 100 | NA | 47.1 | 77.3 | 45.5 |
| PSP 6 | H-cticsrfGw-OH SEQ ID NO: 101 | 40.0 | 44.1 | 76.3 | 22.2 |
| PSP 7 | H-ctksrfhnc-OH SEQ ID NO: 102 | 31.8 | 23.5 | 76.3 | 81.8 |
| PSP 8 | H-ctksrfinc-OH SEQ ID NO: 103 | 90.9 | 79.4 | 83.5 | 90.9 |
| PSP 9 | H-ctksrfknc-OH SEQ ID NO: 104 | 31.8 | 17.6 | 62.9 | NA |
| PSP 10 | H-ctksrflnc-OH SEQ ID NO: 105 | 50 | 88.2 | 82.5 | 95.5 |
| PSP 11 | H-ctksrfmnc-OH SEQ ID NO: 106 | ND | 5.8 | 67 | NA |
| PSP 12 | H-ctksrfnnc-OH SEQ ID NO: 107 | 27.3 | 32.7 | 70.1 | NA |
| PSP 13 | H-ctksrfpnc-OH SEQ ID NO: 108 | 18.2 | 32.7 | 70.1 | 29.6 |
| PSP 14 | H-ctksrfqnc-OH SEQ ID NO: 109 | 18.2 | 23.1 | 62.9 | NA |
| PSP 15 | H-ctksrfrnc-OH SEQ ID NO: 110 | ND | 11.5 | 61.9 | 3.7 |
| PSP 16 | H-ctksrfsnc-OH SEQ ID NO: 111 | 45.5 | 13.5 | 71.1 | NA |
| PSP 17 | H-ctksrftnc-OH SEQ ID NO: 112 | 9.1 | 30.8 | 74.2 | NA |
| PSP 18 | H-ctksrfvnc-OH SEQ ID NO: 113 | 45.5 | 51.9 | 78.4 | 70.4 |
| PSP 19 | H-ctksrfwnc-OH SEQ ID NO: 114 | ND | 28.8 | 78.4 | 92.6 |
| PSP 20 | H-ctksrfync-OH SEQ ID NO: 115 | 63.6 | 73.5 | 81.4 | 95.5 |

NA- No Activity;
ND- Not Determined

In another embodiment, the peptide of the invention has the general formula tX/xsrfin (formula II), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from rrkkctasrfinc, rrkkctcsrfinc, rrkkctdsrfinc, rrkkctesrfinc, rrkkctfsrfinc, rrkkctGsrfinc, rrkkcthsrfinc, rrkkctisrfinc, rrkkctksrfinc, rrkkctlsrfinc, rrkkctmsrfinc, rrkkctnsrfinc, rrkkctpsrfinc, rrkkctqsrfinc, rrkkctrsrfinc, rrkkctssrfinc, rrkkcttsrfinc, rrkkctvsrfinc, rrkkctwsrfinc and rrkkctysrfinc. Activities for these peptides against different influenza viruses are shown in Table 7. Also within the scope of the invention are peptides as shown above wherein the solubility tag is in the L form (RRKK) (SEQ ID NO:156). Also within the scope of the invention are functional derivatives of these peptides which are without any cyclization.

TABLE 7

500 µM of each peptide was screened for their anti-viral activity against various influenza viruses by plaque reduction assay on MDCK cells. Data are presented as the mean value of triplicate measurements.

| 500 µM | | % inhibition | | |
|---|---|---|---|---|
| FPT ID | Sequence | H9N2 | H1N1 | H3N8 |
| PSP II A1 | H-rrkkctasrfinc-OH SEQ ID NO: 116 | 40 | NA | 25.9 |
| PSP II A2 | H-rrkkctcsrfinc-OH SEQ ID NO: 117 | NA | 1.7 | 44.4 |
| PSP II A3 | H-rrkkctdsrfinc-OH SEQ ID NO: 118 | 40 | 44.8 | 85.2 |
| PSP II A4 | H-rrkkctesrfinc-OH SEQ ID NO: 119 | 60 | 36.2 | 74.1 |
| PSP II A5 | H-rrkkctfsrfinc-OH SEQ ID NO: 120 | 50 | 82.8 | 100 |
| PSP II A6 | H-rrkkctGsrfinc-OH SEQ ID NO: 121 | 20 | 1.7 | 44.4 |
| PSP II A7 | H-rrkkcthsrfinc-OH SEQ ID NO: 122 | 50 | 71 | 81.5 |
| PSP II A8 | H-rrkkctisrfinc-OH SEQ ID NO: 123 | 20 | 75 | 77.8 |
| PSP II A9 | H-rrkkctksrfinc-OH SEQ ID NO: 124 | 50 | 81 | 77.8 |
| PSP II A10 | H-rrkkctlsrfinc-OH SEQ ID NO: 125 | 40 | 63.5 | 88.9 |
| PSP II A11 | H-rrkkctmsrfinc-OH SEQ ID NO: 126 | 40 | 65.4 | 76.5 |
| PSP II A12 | H-rrkkctnsrfinc-OH SEQ ID NO: 127 | NA | 53.8 | 70.6 |
| PSP II A13 | H-rrkkctpsrfinc-OH SEQ ID NO: 128 | 70 | 86.5 | 97 |
| PSP II A14 | H-rrkkctqsrfinc-OH SEQ ID NO: 129 | 80 | 73 | 85 |
| PSP II A15 | H-rrkkctrsrfinc-OH SEQ ID NO: 130 | 90 | 57.7 | 79.4 |
| PSP II A16 | H-rrkkctssrfinc-OH SEQ ID NO: 131 | 90 | 61.5 | 61.8 |
| PSP II A17 | H-rrkkcttsrfinc-OH SEQ ID NO: 132 | 80 | 67.3 | 70.6 |

TABLE 7-continued

500 µM of each peptide was screened for their anti-viral activity against various influenza viruses by plaque reduction assay on MDCK cells. Data are presented as the mean value of triplicate measurements.

| 500 µM | | % inhibition | | |
|---|---|---|---|---|
| FPT ID | Sequence | H9N2 | H1N1 | H3N8 |
| PSP II A18 | H-rrkkctvsrfinc-OH SEQ ID NO: 133 | 70 | 42.3 | 47 |
| PSP II A19 | H-rrkkctwsrfinc-OH SEQ ID NO: 134 | 100 | 88.4 | 82.4 |
| PSP II A20 | H-rrkkctysrfinc-OH SEQ ID NO: 135 | CD | CD | CD |
| RRKK-PSP II A19 | H-RRKKctwsrfinc-OH SEQ ID NO: 136 | | | 100 |

CD- Cell Death;
NA- No Activity

In another embodiment, the peptide of the invention has the general formula wwftX/xia (formula IX), where X/x is a, c, d, e, G, h, i, k, l, m, n, p, q, r, s, t, v, w, or y. The peptide may comprise a cysteine residue at the N and C terminal end for cyclisation and/or a solubility tag. In another embodiment, the peptide is selected from RRKKcwwftaiac, RRKKcwwftciac, RRKKcwwftdiac, RRKKcwwfteiac, RRKKcwwftGiac, RRKKcwwfthiac, RRKKcwwftiiac, RRKKcwwftkiac, RRKKcwwftliac, RRKKcwwftmiac, RRKKcwwftniac, RRKKcwwftpiac, RRKKcwwftqiac, RRKKcwwftriac, RRKKcwwftsiac, RRKKcwwftviac, RRKKcwwftwiac, and RRKKcwwftyiac. Activities for these peptides against different influenza viruses are shown in table 8. Also within the scope of the invention are peptides as shown above wherein the solubility tag is in the D form (rrkk). Also within the scope of the invention are functional derivatives of these peptides which are without any cyclization.

TABLE 8

1 µM of each peptide from PSP VII A library was screened for their anti-viral activity against influenza virus (H1N1 A1/Malaysia/302/54) by plaque reduction assay on MDCK cells. Data are presented as the mean value of triplicate measurements.

| Peptide ID | Sequence | % Inhibition |
|---|---|---|
| PSP VII A1 | H-RRKKcwwftaiac-OH SEQ ID NO: 137 | 25.2 |
| PSP VII A2 | H-RRKKcwwftciac-OH SEQ ID NO: 138 | 11.9 |
| PSP VII A3 | H-RRKKcwwftdiac-OH SEQ ID NO: 130 | 9.5 |
| PSP VII A4 | H-RRKKcwwfteiac-OH SEQ ID NO: 140 | 3.8 |
| PSP VII A5 | H-RRKKcwwftGiac-OH SEQ ID NO: 141 | 9.5 |
| PSP VII A7 | H-RRKKcwwfthiac-OH SEQ ID NO: 142 | 47.1 |

TABLE 8-continued

1 μM of each peptide from PSP VII A library was screened for their anti-viral activity against influenza virus (H1N1 A1/Malaysia/302/54) by plaque reduction assay on MDCK cells. Data are presented as the mean value of triplicate measurements.

| Peptide ID | Sequence | % Inhibition |
|---|---|---|
| PSP VII A8 | H-RRKKcwwftiiac-OH SEQ ID NO: 143 | 84.8 |
| PSP VII A9 | H-RRKKcwwftkiac-OH SEQ ID NO: 144 | 17.4 |
| PSP VII A10 | H-RRKKcwwftliac-OH SEQ ID NO: 14 | 35.7 |
| PSP VII A11 | H-RRKKcwwftmiac-OH SEQ ID NO: 146 | 9.8 |
| PSP VII A12 | H-RRKKcwwftniac-OH SEQ ID NO: 147 | 55.2 |
| PSP VII A13 | H-RRKKcwwftpiac-OH SEQ ID NO: 148 | 41.9 |
| PSP VII A14 | H-RRKKcwwftqiac-OH SEQ ID NO: 149 | 21.9 |
| PSP VII A15 | H-RRKKcwwftriac-OH SEQ ID NO: 150 | 39.1 |

In another embodiment, peptides described herein have antiviral activity against at least one, preferably more than one influenza virus that infects humans. In another embodiment, the peptides described herein have antiviral activity against more than one subtype of an influenza virus, preferably one that infects humans. In one example, the influenza virus is influenza A or influenza B virus. The influenza A and/or B virus subtype may be selected from one or more of the subtypes listed in table 9.

TABLE 9

Influenza subtypes.

| ID | Virus | Subtype | Origin |
|---|---|---|---|
| H1N1 | Influenza A1/Malaysia/302/1954 | H1N1 | Human |
| H3N2 | Influenza A/HK/8/1968 | H3N2 | Human |
| 2009 pandemic | Influenza A/NY/18/2009 | H1N1* | Swine |
| H9N2 | Influenza A/Iran/16/2000 | H9N2 | Avian |
| H3N8 | Influenza A/Miami/2/63 | H3N8 | Equine |
| H5N1 | Influenza A/Kampung pasir/5744/2004 | H5N1** | Avian |
| PR8 | Influenza A/PR/8/1934 | H1N1 | Human |
| MA-PR8 | Influenza A/PR/8-MC/1934 | H1N1 | Mouse Adapted |
| IBV | Influenza B/MALAYSIA/2506/04 | | |

*Swine origin 2009 Pandemic influenza strain
**Highly pathogenic avian influenza virus - Pandemic strain It is to be understood that the present invention is not restricted to influenza A viruses and the influenza virus may be any of type A, type B or type C viruses. The virus may be of human or animal origin, for example of avian origin. The preferred viruses are type A influenza viruses, in particular viruses of human origin or human-infective viruses.

Thus, in contrast to C-P1, the peptides of the invention show broad spectrum antiviral activity as they are effective against more than one, preferably 2, 3, 4, 5 or more influenza virus A subtypes.

Furthermore, peptides described herein are more effective against influenza virus than C-P1. The most active peptide of the invention is >30000 times more effective against the avian influenza virus than C-P1.

TABLE 10

$IC_{50}$ values (μM) of the selected FPT peptides against different subtypes of Influenza A virus as assessed by plaque reduction assays

| FPT | H1N1 | H3N2 | 2009 pandemic | H9N2 | H3N8 | H5N1 | PR8 | IBV |
|---|---|---|---|---|---|---|---|---|
| PSP III B5 | 1.6 | 1.4 | 1.17 | 0.9 | 0.15 | 0.22 | 1.2 | nd |
| PSP IV A5 | 0.3 | 0.3 | 1.0 | 0.76 | 0.3 | 0.55 | 0.4 | nd |
| PSP IV A17 | 0.051 | 0.056 | 0.033 | nd | nd | nd | 0.26 | 0.99 |
| PSP V A19 | nd | nd | nd | nd | nd | nd | 0.02 | nd |
| PSP VI A1 | 0.005 | 0.0019 | 0.00013 | 0.0104 | 0.002 | nd | 0.004 | 0.0012 |

TABLE 10-continued

IC$_{50}$ values (µM) of the selected FPT peptides against different subtypes of Influenza A virus as assessed by plaque reduction assays

| FPT | H1N1 | H3N2 | 2009 pandemic | H9N2 | H3N8 | H5N1 | PR8 | IBV |
|---|---|---|---|---|---|---|---|---|
| C-P1 (Comparative example) | nd | nd | nd | >320 | nd | nd | nd | nd |
| Oseltamivir acid (Comparative example) | nd | nd | nd | nd | nd | nd | 0.14 | nd | where NA = not active, and nd = not determined.

The featured peptides and biologically active variants thereof can be modified in numerous ways. For example, agents, including additional amino acid residues, other substituents, and protecting groups can be added to the amino terminus, the carboxy terminus, or both. For example, as described above, the peptides can be modified to include cysteine residues or other sulfur-containing residues or agents that can participate in disulfide bond formation.

The peptides of the invention may also comprise one or more modified amino acids at any position(s) and/or N-terminal and/or C-terminal end to increase the solubility, stability, reactivity or improve other properties. These modifications include the addition of chemical groups such as but not limited to acetyl, carbobenzoyl, dansyl, a t-butyloxycarbonyl group, a 9-fluorenylmethyoxycarbonyl group or a hydrophilic groups to the amino-terminal end and/or t-buyloxycarbonyl, or an amido group or a para-nitrobenzyl ester group or a hydrophilic group to the carboxy-terminal end. They may also comprise modified amide bonds such as N-methylation.

In another embodiment, any of the peptides described herein include one or more substituents. For example, the peptide can include a substituent at the amino-terminus, carboxy-terminus, and/or on a reactive amino acid residue side-chain. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group.

The substituent can be a non-protein polymer, for example, a polyether, a polyethylene glycol (PEG), a polypropylene glycol, or a polyoxyalkylene, a polyalkylene glycol (for example, polypropylene glycol (PPG), a polybuylene glycol (PBG), or a PPG-PEG block/random polymer).

The non-protein polymer can vary in size and shape. For example, any of the non-protein polymers listed above (e.g., PEG) can be linear, branched, or comb-shaped. Regarding size, the molecular weight can vary. For example, the PEG can have a molecular weight of, for example, about 300 Da, about 1000 Da, about 2000 Da, about 3000 Da, about 4000 Da, about 5000 Da, about 6000 Da, about 7000 Da, about 8000 Da, about 9000 Da, about 10000 Da, about 11,000 Da, about 12000 Da about 13000 Da about 14000 Da about 15000 Da, about 20000 Da, about 30000 Da, about 40000 Da, or about 50000 Da. For example, the PEG can be of a molecular weight anywhere in between 300 DA and 2000 Da, 300 Da and 3000 Da, 1000 Da and 2000 Da and 1000 and 3000 Da. The non-protein polymer (e.g., PEG) can be linked to the peptide by any number of functional group chemistries (e.g., carboxylated-mPEGs, p-nitrophenyl-PEGs, aldehyde-PEGs, amino-PEGs, thiol-PEGs, maleimide-PEGs, aminoxy-PEGs, hydrazine-PEGs, tosyl-PEGs, iodoacetamide-PEGs, succiminidylsuccinate-PEGs, succinimidylglutarate-PEGS, succinimidylcarboxypentyl-PEGs, p-nitrophenylcarbonate-PEGs, or ethanethiol-PEGs).

The non-protein polymer (e.g., PEG) can be linked to the peptide through any number of chemical groups including, but not limited to, amino-terminal amino acids, carboxy-terminal amino acids, free amines, and free sulfhydryl groups.

The non-protein polymer (e.g., PEG) may be a functionalized (for example, a monofunctional activated linear PEG, a homobifunctional activated linear PEG, a heterobifunctional activated linear PEG, a multiarmed activated PEG (e.g. 2-armed, 4-armed, 8-armed, etc.), a branched activated PEG and a comb-shaped activated PEG).

The anti-viral peptides of the invention may also comprise a reactive tag at their terminal amino acids for the purpose of detection, isolation, purification etc. These tags may include (but are not limited to) biotin, histidine, GST etc. Suitable tags are known in the art.

The peptides of the invention may also be linked with lipids (phospholipids) or Poly Ethylene Glycol to enhance/alter the solubility, proteolytic stability or other properties and or activity. Therefore, the peptides of the invention include such lipopeptides.

As used herein, the antiviral peptides of the invention may include a mimetic or peptidomimetic derivative which is a compound capable of mimicking the core structure of a peptide. Similarly, it is to be understood that the antiviral peptides may include one or more amino acid replacements, such as isosteres or bioisosteres.

In another embodiment, the antiviral peptides of the invention may be in multimeric form. The multimer could be a dimer, trimer or a tetramer; preferably a dimer. The monomeric antiviral peptides forming the multimer may be made up of the same or different peptides. In preferred embodiments, the peptides forming the multimer are covalently linked.

In another embodiment, the antiviral peptides of the invention may be presented in different physical forms. The physical form could be crystalline, amorphous or other which are well known in the art.

Various examples provided in this patent application demonstrate that the FPTs with substituted amino acids retain the antiviral activity as shown in various sequences described in Tables 2-8. Such derivatives are within the scope of this invention. In another embodiment, the amino acids of the antiviral peptides of the present invention may be substituted with conservative substitutions. Conservative substitution refers to replacement of amino acids with alternative amino acids which may alter the primary sequence but not the function. Examples of conservative amino acid substitutions include: valine, isoleucine and leucine; lysine and arginine; asparagine and glutamine; serine and threonine; glycine and alanine; phenylalanine and tyrosine and aspartic acid and glutamic acid. An amino acid within a given group may be conservatively substituted with another amino acid from the same group.

In another embodiment, the amino acids of the antiviral peptides of the present invention may be replaced with non-natural or unnatural amino acids and their derivatives including, but not limited to, β-amino acids (β3 and β2), Homo-amino acids, Proline and Pyruvic acid derivatives, 3-substituted Alanine derivatives, Glycine derivatives, Ring-substituted Phenylalanine and Tyrosine Derivatives, N-methyl amino acids and others which are well known in the art.

Peptides of the invention or derivatives thereof can be tested for their anti-viral activity using the methods as explained in the following Examples.

The disclosed peptides and their derivatives can be synthesized via any common methods used in peptide synthesis such as liquid phase or solid phase synthesis or any other methods well known in the art.

The peptides of the invention exhibit broad spectrum antiviral activity against influenza A viruses including human, animal subtypes and avian (such as the highly pathogenic H5N1). Illnesses resulting from the infection of these viruses can therefore be treated with the peptides of the invention which can be formulated into pharmaceutically acceptable compositions for such treatment.

Thus, according to another aspect of the invention, one or more peptide of the invention as described above may be formulated into a pharmaceutical composition. This composition may include at least one peptide of the invention together with one or more pharmaceutically acceptable carriers, including excipients, such as diluents, carriers and the like, and additives, such as stabilizing agents, preservatives, solubilizing agents, buffers and the like, as may be desired. A pharmaceutically acceptable carrier is a compound with which a peptide of the present invention may be administered and which contains one or more non-toxic ingredients which do not inhibit or reduce the effectiveness of the active antiviral peptide described herein.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, for example, inhalatory administration.

Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In another embodiment, when administered to an animal, the peptide of the present invention or compositions and pharmaceutically acceptable carriers are sterile. Water is a preferred carrier when the peptides of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

In another embodiment, specific non-limiting examples of carriers and excipients include but are not limited to water, saline, dextrose, glycerol, ethanol, or the like or combinations thereof. Formulation excipients may include polyvinylpyrrolidone, gelatin, hydroxyl cellulose, acacia, polyethylene glycol, mannitol, sodium chloride or sodium citrate.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

For topical administration formulations, any of a variety of creams, ointments, gels, lotions and the like may be employed.

When intended for oral administration, the composition is preferably in solid or liquid form, where semi-solid, semi-liquid, suspension and gel forms are included within the forms considered herein as either solid or liquid.

The composition can be in the form of a liquid, e. g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included. Water containing at least one or more buffering constituents is preferred along with or without stabilizing agents, preservatives and solubilizing agents. When the composition is in the form of a capsule (e. g. a gelatin capsule), it can contain, in addition to materials of the above type, a liquid carrier such as polyethylene glycol, cyclodextrin or a fatty oil.

For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

It is to be understood that any suitable route of administration or delivery method may be used with the peptides described herein, including but not limited to oral, parenteral, depot, buccal, and the like.

In certain embodiments the peptide(s) are formulated with a non-covalent carrier. Non-covalent carriers are well known to those of skill in the art.

In certain embodiments, the peptide(s) are complexed with carriers such as lipids or formulated in liposomes, biodegradable or non-biodegradable microparticles, microcapsules, microspheres and nanoparticles. Methods of producing liposomes, microparticles, microcapsules, microspheres and nanoparticles and complexing or encapsulating compounds therein are well known to those of skill in the art.

In certain embodiments the antiviral peptide(s) described herein are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm.

Illustrative oil in water (O/W) and/or water in oil (W/O) nanoemulsions include, but are not limited to:

1) Surfactant micelles—micelles composed of small molecules surfactants or detergents (e.g., SDS/PBS/2-propanol) which are suitable for predominantly hydrophobic peptides;

2) Polymer micelles—micelles composed of polymer, copolymer, or block copolymer surfactants (e.g., Pluronic L64/PBS/2-propanol) which are suitable for predominantly hydrophobic peptides;

3) Blended micelles: micelles in which there is more than one surfactant component or in which one of the liquid phases (generally an alcohol or fatty acid compound) participates in the formation of the micelle (e.g., Octanoic acid/PBS/EtOH) which are suitable for predominantly hydrophobic peptides;

4) Integral peptide micelles~blended micelles in which the peptide serves as an auxiliary surfactant, forming an integral part of the micelle (e.g., amphipathic peptide/PBS/mineral oil) which are suitable for amphipathic peptides; and 5) Pickering (solid phase) emulsions~emulsions in which the peptides are associated with the exterior of a solid nanoparticle (e.g., polystyrene nanoparticles/PBS/no oil phase) which are suitable for amphipathic peptides.

In another embodiment, the invention relates to a peptide or composition of the invention for use as a medicament.

In another embodiment, the invention relates to a peptide or composition of the invention for use in the treatment of influenza virus infection. In another embodiment, the use is in treating infection of more than one influenza virus. In another embodiment, the influenza virus is influenza virus A and the use is in the treatment of infection of more than one influenza virus A subtype.

In another embodiment, the invention relates to the use of an isolated anti-viral peptide or composition of the invention in the manufacture of a medicament for the treatment of influenza virus infection. In another embodiment, the use is in treating infection of more than one influenza virus. In another embodiment, the influenza virus is influenza virus A and the use is in the treatment of infection of more than one influenza virus A subtype.

In another embodiment, the invention relates to method for treating influenza virus infection comprising administering a therapeutically effective amount of anti-viral peptide or composition of the invention. In another embodiment, the method is for treating infection of more than one influenza virus. In another embodiment, the influenza virus is influenza virus A and the method is for the treatment of infection of more than one influenza virus A subtype.

Also within the scope of the invention are uses and methods described above for prevention of viral infection with an influenza virus.

Administration of the peptides and compositions of the present invention include without limitation oral, topical, parenteral, sublingual, rectal, vaginal, ocular, pulmonary (inhalation) and intranasal. Parenteral administration includes subcutaneous injections, intravenous, intramuscular, intrasternal injection or infusion techniques. Preferably, the compositions are administered parenterally, pulmonary or orally. Pharmaceutical compositions of the invention can be formulated so as to allow a peptide of the present invention to be bioavailable upon administration of the composition to an animal, preferably human. Compositions can take the form of one or more dosage units, where for example, a tablet can be a single dosage unit, and a container comprising a peptide of the present invention in aerosol form can hold a plurality of dosage units.

Parenteral administration includes, but is not limited to, intradermal, intramuscular, intraperitoneal, intravenous, subcutaneous, intranasal, epidural, intracerebral, intraventricular, intrathecal, intravaginal or transdermal. The preferred mode of administration is left to the discretion of the practitioner, and will depend in part upon the site of the medical condition.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The peptides or compositions are administered in a therapeutically effective amount. The terms "therapeutically effective amount" or "pharmaceutically effective amount" refer to the amount and/or dosage, and/or dosage regime of one or more compounds necessary to bring about the desired result e.g., an amount sufficient to reduce or block propagation of a virus, or an amount sufficient to lessen the severity or delay the progression of a symptoms of the viral disease (e.g., therapeutically effective amounts), an amount sufficient to reduce the risk or delaying the onset, and/or reduce the ultimate severity of a disease caused by a viral infection (e.g., prophylactically effective amounts).

The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a peptide of the present invention by weight of the composition. When intended for oral administration, this amount can be varied to range from about 0.1% to about 80% by weight of the composition. Preferred oral compositions can comprise from about 4% to about 50% of the peptide of the present invention by weight of the composition.

Preferred compositions of the present invention are prepared so that a parenteral dosage unit contains from about 0.01% to about 2% or more by weight of the peptide of the present invention.

For intravenous administration, the composition can comprise from about typically about 0.1 mg/day to about 250 mg/day, preferably, between about 0.1 mg/day and about 50 mg/day.

The peptide may be administered therapeutically or prophylactically. Suitable treatment is given 1-4 times daily and preferably continued for 1-7 days or more. The terms "treatment", "treating", or "treat" as used herein, refer to actions that produce a desirable effect on the symptoms or pathology of a disease or condition, particularly those that can be effected utilizing the peptides described herein, and may include, but are not limited to, even minimal changes or improvements in one or more measurable markers of the disease or condition being treated. Treatment also refers to delaying the onset of, retarding or reversing the progress of, reducing the severity of, or alleviating or preventing either the disease or condition to which the term applies, or one or more symptoms of such disease or condition. "Treatment", "treating", or "treat" does not necessarily indicate complete eradication or cure of the disease or condition, or associated symptoms thereof.

In another embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The peptides or compositions of the present invention can be administered by any convenient route, for example by infusion or bolus injection, by absorption through epithelial or mucocutaneous linings.

Pulmonary administration can also be employed, e. g. by use of an inhaler or nebulizer, and formulation with an aerosolizing agent, or via perfusion in a fluorocarbon or synthetic pulmonary surfactant. In certain embodiments, the peptide of the present invention or compositions can be formulated as a suppository, with traditional binders and carriers such as triglycerides.

As explained above, depending on the route of administration, the anti-viral peptides of the invention may be formulated by any means known in the art, including but not limited to tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art.

Administration may also be together with another active compound, for example another antiviral compound. More than one peptide of the invention may also be administered.

Peptides described herein can also be provided as pharmaceutically acceptable salts. A "pharmaceutically acceptable salt" includes a salt with an inorganic base (for example, alkali metals such as sodium or potassium; alkaline earth metals such as calcium and magnesium or aluminium; and ammonia), organic base (for example, trimethylamine, triethylamine, pyridine, picoline, ethanolamine, diethanolamine, and triethanolamine), inorganic acid (for example, hydrochloric acid, hydroboric acid, nitric acid, sulfuric acid, and phosphoric acid) or organic acid (for example, formic acid, acetic acid, Trifluoroacetic acid, fumaric acid, oxalic acid, tartaric acid, maleic acid, citric acid, succinic acid, malic acid, methanesulfonic acid, benzenesulfonic acid and p-toluenesulfonic acid). The examples cited herein are non-limiting.

The invention also relates to a kit comprising a peptide or composition of the invention and instructions for use and optionally adjuvants.

The invention also relates to a screening method for detecting a peptide that has antiviral activity against influenza comprising making a derivative of an isolated anti-viral peptide described herein, exposing the peptide to said virus and screening for antiviral activity.

The invention also relates to an isolated nucleic acid molecule, including a DNA or RNA molecule, encoding an anti-viral peptide of the invention. In another embodiment, the isolated nucleic acid is not naturally occurring.

The invention also relates to a vector comprising a nucleic acid encoding an anti-viral peptide of the invention. The vector may be an expression vector, especially for expression in eukaryotic cells. Such vectors can, for example, be viral, plasmid, cosmid, or artificial chromosome (e.g., yeast artificial chromosome) vectors.

The vectors described herein can be introduced into cells or tissues by any one of a variety of known methods within the art. Such methods are described for example in Sambrook et al., Molecular Cloning: A Laboratory Manual, Cold Spring Harbor, 4th edition (Jun. 15, 2012).

The invention also relates to a host cell comprising an anti-influenza peptide of the invention.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known in the art.

Thus, in the present invention, cells can be transfected in vitro or ex vivo, and the expressed peptide can be isolated therefrom by methods known in the art. The cells can also be administered to a subject or, alternatively, cells can be directly modified in vivo.

The invention also relates to a combination comprising an anti-influenza peptide of the invention and a second agent selected, for example selected from a nucleic acid, peptide, protein, contrast agent, antibody, toxin and small molecule.

The invention also relates to a recombinant library, for example a phage library, comprising a peptide of the invention.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure. The specifics of these examples should not be treated as limiting.

Each document cited herein is incorporated herein by reference in its entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

EXAMPLES

The following non-limiting examples are provided to further illustrate the present invention.

Example 1. Materials and Methods

Cell culture and virus: A/PR/8/1934 (H1N1), A1/Mal/302/1954 (H1N1), A/chicken/Iran/16/2000 (H9N2) and A/equine/2/Miami/63 (H3N8) is propagated in 8 days old, specific pathogen-free embryonated chicken eggs at 35° C. or 37° C. for 48 hrs. A/NY/18/2009 (2009 pandemic H1N1), A/HK/8/1968 (H3N2) and A/Kampung Pasir/5744/2004 (H5N1) are propagated in MDCK cells. The propagation and purification methods are adapted and modified from Yusoff et al (Yusoff et al., 1996). Briefly, viruses are either propagated in embryonated chicken eggs or MDCK cells. In case of embryonated chicken based propagation, viruses are injected into 8 or 9 days old specific pathogen free embryonated chicken eggs. After 48 hrs incubation at 37° C., the allantoic fluid is harvested and clarified by centrifugation (30 min, 12,096×g, 4° C.). The virus is purified from the clarified supernatants by 30%-60% sucrose gradient ultracentrifugation (3.5 hrs, 285,000×g, and 4° C.) and used in the studies below. In case of cell culture based propagation, the viruses at 1.0 m.o.i are infected in MDCK cells grown overnight and incubated at 37° C., 5% $CO_2$ until 50-70% CPE appears. Supernatants are collected and processed as explained above.

Peptide Synthesis: Peptides are synthesized by Mimotopes (Australia) or Polypeptides Inc. (USA) using a solid state method. The sequences of illustrative peptides are listed in Table 1-8. Initially peptides are synthesized in smaller amounts as a library and specific peptides from the library with significant anti-viral activity are synthesized on a larger scale to determine the $IC_{50}$ values against various subtypes of the viruses. Peptides are purified by HPLC (with more than >95 purity) and the sequences are confirmed by Mass spectrometer analysis. The sequence "RRKK" (or "rrkk") is optionally added to the N terminal end of all peptides to increase the solubility. All the peptides are synthesized using dextro-amino acids or levo-amino acids, depending upon the sequence.

Plaque reduction assay: Plaque reduction assay is performed to determine the anti-viral activity of selected peptides. Peptides at various concentrations and influenza virus (~80-120 PFU) are pre-mixed and incubated for 90 mins at 4° C. or on ice. Confluent monolayers of MDCK cells (600,000 cells per well) seeded in 6-well plates are washed twice using 1×PBS (Phosphate buffered saline) and added with peptide-virus mixture, allowed for absorption for 1 hr at 37° C. or 35° C. in 5% $CO_2$. Unbound viruses are removed by washing with PBS and each well is overlaid with 2 ml of 0.6% low-melting point agarose in 1×DMEM supplemented with 2 µg/ml Tosylsulfonyl phenylalanyl chloromethyl ketone (TPCK)-treated trypsin (Sigma, St. Louis, Mo.). Plates are incubated at 37° C. or 35° C. in 5% $CO_2$ for 41 to 68 hrs or until clear plaques appeared. The plaques are stained using 0.1% crystal violet stain (Merck, Germany) and counted.

Alanine Scanning: Purified viruses are quantified by Bradford assay (Thermo Scientific, US). 15 µg/well of purified virus is coated onto 96-well ELISA microplate (eppendorf, US) overnight at 4° C. Coated wells are washed twice with 1×PBST (Phosphate buffered saline with Tween-20) and blocked with 5 mg/ml BSA in 1×PBS at room temperature for 1 hr. The coated wells are incubated with 150 µM biotin conjugated peptides in 1% BSA (Bovine serum albumin)/1×PBST for 2 hr at room temperature. After three washes using 1×PBST, the biotin conjugated peptides are detected using primary anti-biotin rabbit (Cell Signaling 1:250, MA) and HRP conjugated anti-rabbit secondary antibodies (Abcam 1:5000, MA). The absorbance is read on Biorad iMark microplate reader at 415 nm.

Hemagglutination assay: Hemagglutination of chicken Red Blood Cells (cRBCs) are carried out in V-bottom 96 well microtiter plates as explained in Jones et al., Journal of Virology, 80 (24):11960-11967 (2006).

Bradford Assay: Protein quantification is done with Coomassie (Bradford) Protein assay kit (Thermo scientific, USA) as per manufacturer's instructions.

Laboratory facilities: All works with H5N1 viruses are carried out at biosafety level 3+ certified containment laboratories, certified for such use by authorities at Universiti Putra Malaysia, Malaysia. The researchers are requested to wear appropriate protective equipment and clothes.

$IC_{50}$ Calculation: All experiments are done in triplicates and the data represents the results of at least three independent determinations. The $IC_{50}$ values are calculated based on dose-response curves as analyzed by Graphpad Prism™ software.

Cytotoxicity Assay: MDCK cells or A549 cells (~5000 cells/well) are grown overnight on 96 well plates. The media is replaced by serially diluted peptides and incubated again for 24/48 h. The culture medium is removed and 20 µl of CellTiter 96® AQueous One Solution [3-(4,5-dimethylthiozol-2-yl)-3,5-dipheryl tetrazolium bromide] (Promega, WI, USA) is added and incubated at 37° C. for 2 h. The optical density is measured at 490 nm in an microplate reader (iMARK, BioRad, USA).

Hemolytic Assay: Freshly obtained human red blood cells are washed with PBS (pH 7.4) buffer for three times by centrifugation at 500×g for 10 minutes. Peptides are incubated with the wash RBCs in a V-bottom microtiter plate for 1 hour. 1% Triton X-100 is used as positive control. After the incubation, the plate is centrifuged at 500×g for 5 minutes and the supernatants are transferred to a fresh clear bottom 96 well plate and the absorbance of the is measured at 545 nm with iMark microplate reader (Biorad, USA).

Example 2

Anti-viral activity of FPTs in vitro: In this example, anti-viral activity of the derivatives of C-P1 peptide against various subtypes of influenza viruses is tested. A retro-inverso version of the C-P1 i.e. P1-RI-CD is synthesized to make the peptide protease resistance. The P1-RI-CD is subjected to alanine scanning to identify one or more amino acids which are not essential for the peptide's anti-viral activity. From P1-RI-CD, a series of peptides are synthesized with replaced amino acids at a single position which is earlier identified as one of the non-essential amino acids for the anti-viral activity through the above mentioned alanine scanning. The identified non-essential amino acid at the mentioned position of P1-RI-CD is replaced with the remaining 19 proteinogenic amino acids, one at a time, and their activities are evaluated with the plaque reduction assay. Tables 1-8 show the sequences of evaluated peptides. Starting from the PSP IIA library a tetra-peptide solubility tag comprising Arginine and Lysine amino acids are added at the amino terminal end either in dextro or in levo form. A plaque reduction assay is performed as explained above in materials and methods section. Briefly, viruses are treated with PBS alone (mock) or various concentrations of FPT for 1 hour at 4° C. and added on to the confluent monolayer of MDCK cells for 1 hour for absorption. After the absorption, the monolayer is overlaid with agarose and incubated further until the plaques appeared. The number of plaques is counted after 24 hours-72 hours (depending on the plaque forming abilities of different virus subtypes) and the $IC_{50}$ values are calculated using Prism software. As shown in FIGS. 1A-1F and FIGS. 2-4, FPTs effectively inhibited the multiplication of various sub-types of influenza viruses in a dose dependent manner.

Example 3

Anti-viral activity of FPTs in vivo: In this example, the anti-viral activity of one of FPTs i.e. PSP IVA-17 is evaluated against mouse adapted influenza A H1N1 virus in 6 weeks old BALB/c female mice.

Initially, the mice are anesthetized with ketamine xylazine solution and administered with different pfu of the above said virus and the clinical symptoms are observed for a number of days to select optimal challenge dose. Once, the optimal challenge dose is selected, the mice are intranasally challenged with the optimal dose of virus (H1N1 A/PR/8-MC/1934) followed by intravenous administration of 3.5 mg/kg/day of PSP IV A17 peptide for 7 days. The first dose is administered one hour pre-infection and the subsequent doses are administered every 24 hours. The prognosis and the diseases progress are measured based on clinical symptoms such as body weight, ruffled fur, hunched posture, body shivering, paralysis and little or no movement. The mice are monitored daily for 21 consecutive days from the day of infection. Mouse mortality is decided by more than 20% weight loss and severe ruffled fur. As observed in the FIG. 5, PSP IV A17 completely inhibited the morbidity of the influenza treated mice.

Example 4

Effect of Anti-viral peptides on Hemagglutination activity: In this example, anti-viral peptides are tested for its ability to inhibit hemagglutination of influenza viruses to infer whether the peptides inhibit the virus replication by attaching to HA protein of the viruses. The experiment is carried out as explained in the example 1. Briefly, 10 μM of peptide is mixed with 4HAU/50 μl PR/8 virus and the HA activity is measured with chicken Red Blood Cells. No inhibition of hemagglutination activity was observed with the peptide treatment.

Example 5

Cytotoxic effects of FPTs on human hepatocytes: The cytotoxic effects of anti-viral peptides on human hepatic cell HepaRG™, a cell with a proven differentiated hepatocyte phenotype under the cell-culture conditions, are analyzed by AvantiCell Science Ltd, UK Briefly, cytotoxicity of the test materials is measured as the release of cytosolic contents, specifically cytosolic dehydrogenases, during a 24-hour challenge. Cell-content release into culture medium is measured by a sensitive fluorescence-based assay. Assay performance was monitored by the use of negative controls (test material solvents) and positive controls in the form of known cytotoxic agents. At the end of the challenge period, the assay readout is generated by a standard methodology, and results are calculated as percentage cell lysis (% lysis), by comparing test measurements with that generated by a fully-lysed detergent-treated control (100% lysis).

Example 6

Electron microscopic analysis: The PSP VI A12 peptide treated or untreated viruses H1N1 (A/PR/8/1934) is attached to a carbon-coated grid (Formvar carbon films on Copper; Agar Scientific, UK) and negatively stained with 3% Uranyl acetate and analyzed using a Transmission Electron Microscope (LEO 912 Advance Biology Filter).

Example 7

Cytotoxic effects of anti-viral peptides on MDCK cells or A549 cells: The cytotoxic effects of anti-viral peptides are shown in FIGS. 7A & 7B which are assessed as explained in Example 1. Briefly, the MDCK cells/A549 cells are treated with either 0 μM peptide (Mock) or increasing concentrations (i.e., 0.1 μM, 0.3 μM, 1 μM, 3 μM, 10 μM, 30 μM and 100 μM) of PSP V A19 and PSP VI A1 and the cell death is determined by 48 hours post infection by a cytotoxicity assay with CellTiter 96® $Aq_{ueous}$ One Solution cell proliferation assay kit (Promega, USA) as explained by manufacturer. The results are normalized to the mock treated cells. As shown in the results, the PSP V A19 and PSP VI A1 showed no significant toxicity against MDCK cells/A549 cells with $CE_{50}$ (Cytotoxic Effect 50) value more than 30 μM.

Example 8

Hemolytic activities of FPTs: The hemolytic effects of the anti-viral peptides are shown in FIG. 8 which was assessed as explained in Example 1. Briefly, different concentrations of the peptides are incubated with human red blood cells and the hemolysis is determined at one hour post incubation by the absorbance of released hemoglobin in the supernatant at 545 nm with Biorad iMark microplate reader.

REFERENCES

Beare A S, W. R. (1991). Replication of avian influenza viruses in humans. *Archives of Virology* 119, 37-42.

Echevarria-Zuno, S., Mejia-Arangure, J. M., Mar-Obeso, A. J., Grajales-Muniz, C., Robles-Perez, E., Gonzalez-Leon, M., Ortega-Alvarez, M. C., Gonzalez-Bonilla, C., Rascon-Pacheco, R. A., and Borja-Aburto, V. H. (2009). Infection and death from influenza A H1N1 virus in Mexico: a retrospective analysis. *Lancet* 374(9707), 2072-9.

Gao, R., Cao, B., Hu, Y., Feng, Z., Wang, D., Hu, W., Chen, J., Jie, Z., Qiu, H., Xu, K., Xu, X., Lu, H., Zhu, W., Gao, Z., Xiang, N., Shen, Y., He, Z., Gu, Y., Zhang, Z., Yang, Y., Zhao, X., Zhou, L., Li, X., Zou, S., Zhang, Y., Yang, L., Guo, J., Dong, J., Li, Q., Dong, L., Zhu, Y., Bai, T., Wang, S., Hao, P., Yang, W., Han, J., Yu, H., Li, D., Gao, G. F., Wu, G., Wang, Y., Yuan, Z., and Shu, Y. (2013). Human Infection with a Novel Avian-Origin Influenza A (H7N9) Virus. *N Engl J Med*.

Gonzalez-Rey, E., Varela, N., Sheibanie, A. F., Chorny, A., Ganea, D., and Delgado, M. (2006). Cortistatin, an anti-inflammatory peptide with therapeutic action in inflammatory bowel disease. *Proc Natl Acad Sci USA* 103(11), 4228-33.

Gordon, Y. J., Romanowski, E. G., and McDermott, A. M. (2005). A review of antimicrobial peptides and their therapeutic potential as anti-infective drugs. *Curr Eye Res* 30(7), 505-15.

Hama, R., Jones, M., Okushima, H., Kitao, M., Noda, N., Hayashi, K., and Sakaguchi, K. (2011). Oseltamivir and early deterioration leading to death: a proportional mortality study for 2009A/H1N1 influenza. *Int J Risk Saf Med* 23(4), 201-15.

Hummel, G., Reineke, U., and Reimer, U. (2006). Translating peptides into small molecules. *Mol Biosyst* 2(10), 499-508.

Janin, Y. L. (2003). Peptides with anticancer use or potential. *Amino Acids* 25(1), 1-40.

Jones, J. C., Turpin, E. A., Bultmann, H., Brandt, C. R., and Schultz-Cherry, S. (2006). Inhibition of influenza virus infection by a novel antiviral peptide that targets viral attachment to cells. *J Virol* 80(24), 11960-7.

Kilbourne, E. D. (2006). Influenza pandemics of the 20th century. *Emerg Infect Dis* 12(1), 9-14.

Kim, C. U., Lew, W., Williams, M. A., Liu, H., Zhang, L., Swaminathan, S., Bischofberger, N., Chen, M. S., Mendel, D. B., Tai, C. Y., Laver, W. G., and Stevens, R. C. (1997). Influenza neuraminidase inhibitors possessing a novel hydrophobic interaction in the enzyme active site: design, synthesis, and structural analysis of carbocyclic sialic acid analogues with potent anti-influenza activity. *J Am Chem Soc* 119(4), 681-90.

Kola, I., and Landis, J. (2004). Can the pharmaceutical industry reduce attrition rates? *Nat Rev Drug Discov* 3(8), 711-5.

Kolocouris, N., Zoidis, G., Foscolos, G. B., Fytas, G., Prathalingham, S. R., Kelly, J. M., Naesens, L., and De Clercq, E. (2007). Design and synthesis of bioactive adamantane spiro heterocycles. *Bioorg Med Chem Lett* 17(15), 4358-62.

Ladner, R. C., Sato, A. K., Gorzelany, J., and de Souza, M. (2004). Phage display-derived peptides as therapeutic alternatives to antibodies. *Drug Discov Today* 9(12), 525-9.

Loffet, A. (2002). Peptides as drugs: is there a market? *J Pept Sci* 8(1), 1-7.

McGregor, D. P. (2008). Discovering and improving novel peptide therapeutics. *Curr Opin Pharmacol* 8(5), 616-9.

McKimm-Breschkin, J. L. (2000). Resistance of influenza viruses to neuraminidase inhibitors—a review. *Antiviral Res* 47(1), 1-17.

Perez, J. T., Varble, A., Sachidanandam, R., Zlatev, I., Manoharan, M., Garcia-Sastre, A., and tenOever, B. R. (2010). Influenza A virus-generated small RNAs regulate the switch from transcription to replication. *Proc Natl Acad Sci USA* 107(25), 11525-30.

Peter F Wright, G. N., Yoshihiro Kawaoka (2007). Orthomyxoviruses. In "Fields Virology" (P. M. H. David M Knipe, Ed.), Vol. 2, pp. 1692. 2 vols. Lippincott Williams & Wilkins, Philadelphia, Pa.

Peter Palese, M. L. S. (2007). Orthomyxoviridae: The viruses and their replication. In "Fields Virology" (P. M. H. David M Knipe, Ed.), Vol. 2, pp. 1647. 2 vols. Lippincott Williams & Wilkins, Philadelphia, Pa.

Stiver, G. (2003). The treatment of influenza with antiviral drugs. *CMAJ* 168(1), 49-56.

Ungchusak, K., Auewarakul, P., Dowell, S. F., Kitphati, R., Auwanit, W., Puthavathana, P., Uiprasertkul, M., Boonnak, K., Pittayawonganon, C., Cox, N. J., Zaki, S. R., Thawatsupha, P., Chittaganpitch, M., Khontong, R., Simmerman, J. M., and Chunsutthiwat, S. (2005). Probable person-to-person transmission of avian influenza A (H5N1). *N Engl J Med* 352(4), 333-40.

Vlieghe, P., Lisowski, V., Martinez, J., and Khrestchatisky, M. (2010). Synthetic therapeutic peptides: science and market. *Drug Discov Today* 15(1-2), 40-56.

von Itzstein, M., Wu, W. Y., Kok, G. B., Pegg, M. S., Dyason, J. C., Jin, B., Van Phan, T., Smythe, M. L., White, H. F., Oliver, S. W., and et al. (1993). Rational design of potent sialidase-based inhibitors of influenza virus replication. *Nature* 363(6428), 418-23.

Webster, R. G., and Govorkova, E. A. (2006). H5N1 influenza—continuing evolution and spread. *N Engl J Med* 355(21), 2174-7.

Whitley, R. J., Boucher, C. A., Lina, B., Nguyen-Van-Tam, J. S., Osterhaus, A., Schutten, M., and Monto, A. S. (2013). Global Assessment of Resistance to Neuraminidase Inhibitors: 2008-2011. The Influenza Resistance Information Study (IRIS). *Clin Infect Dis*.

Yang, Y., Halloran, M. E., Sugimoto, J. D., and Longini, I. M., Jr. (2007). Detecting human-to-human transmission of avian influenza A (H5N1). *Emerg Infect Dis* 13(9), 1348-53.

Yun, N. E., Linde, N. S., Zacks, M. A., Barr, I. G., Hurt, A. C., Smith, J. N., Dziuba, N., Holbrook, M. R., Zhang, L., Kilpatrick, J. M., Arnold, C. S., and Paessler, S. (2008). Injectable peramivir mitigates disease and promotes survival in ferrets and mice infected with the highly virulent influenza virus, A/Vietnam/1203/04 (H5N1). *Virology* 374(1), 198-209.

Yusoff, K., Tan, W. S., Lau, C. H., Ng, B. K., and Ibrahim, A. L. (1996). Sequence of the haemagglutinin-neuraminidase gene of the Newcastle disease virus oral vaccine strain V4(UPM). *Avian Pathol* 25(4), 837-44.

Zhirnov, O. P., and Klenk, H. D. (2011). [Aprotinin-induced inhibition of pandemic influenza virus A(H1N1) reproduction]. *Vopr Virusol* 56(3), 24-8.

What is claimed is:

1. An isolated peptide comprising the sequence A1-A2-A3-A4-A5-A6-A7, where A1 is t or w, A2 is k or w, A3 is s or f, A4 is r or t, A5 is f, h, n, or w, A6 is i or d, and A7 is n or a, and where one of A1, A2, A3, A4, A5, A6, or A7 is optionally replaced with another D-amino acid or L-amino acid.

2. The peptide of claim 1 comprising the sequence wwftfia or twftfin.

3. The peptide of claim 1 comprising the sequence tksrfdn.

4. The peptide of claim 1 comprising the sequence tksrfxn, where x is i, l, or y.

5. The peptide of claim 1 comprising the sequence twf(x2)fin, where (x2) is i, l, m, r, s, t, v, or w.

6. The peptide of claim 1 comprising the sequence-tw(x3)rfin, where (x3) is a, c, e, f, G, h, i, k, l, m, n, p, q, r, s, t, v, w, or y.

7. The peptide of claim 1 comprising the sequence-t(x4)srfin, where (x4) is p, r, s, or w.

8. The peptide of claim 1 comprising the sequence (x5)wftfin, where (x5) is m or w.

9. The peptide of claim 1 comprising a sequence selected from tksrfX/xn, tX/xsrfin, twX/xrfin, twfX/xfin, X/xwftfin, wwftfiX/x, wwftX/xia and tksrfdn, where X/x is a D-amino acid or an L-amino acid.

10. The peptide of claim 1 further comprising a cysteine residue at the N terminus and a cysteine residue at the C terminus of the sequence.

11. The peptide of claim 10 wherein the two cysteine residues form a cycle.

12. The peptide of claim 1 further comprising a solubility tag attached to the N or C terminus.

13. The peptide of claim 1 further comprising RRKK or rrkk attached to the N or C terminus as a solubility tag.

14. The peptide of claim 1 wherein said peptide is selected from RRKKctwarfinc, RRKKctwcrfinc, RRKKctwdrfinc, RRKKctwerfinc, RRKKctwfrfinc, RRKKctwGrfinc, RRKKctwhrfinc, RRKKctwirfinc, RRKKctwkrfinc, RRKKctwlrfinc, RRKKctwmrfinc, RRKKctwnrfinc, RRKKctwprfinc, RRKKctwqrfinc, RRKKctwrrfinc, RRKKctwsrfinc, RRKKctwtrfinc, RRKKctwvrfinc, RRKKctwwrfinc and RRKKctwyrfinc.

15. The peptide of claim 1 wherein said peptide is selected from RRKKctwfafinc, RRKKctwfcfinc, RRKKctwfdfinc, RRKKctwfefinc, RRKKctwfffinc, RRKKctwfGfinc, RRKKctwfufinc, RRKKctwfifinc, RRKKctwfkfinc, RRKKctwflfinc, RRKKctwfmfinc, RRKKctwfnfinc, RRKKctwfpfinc, RRKKctwf-qfinc, RRKKctwfrfinc, RRKKctwfsfinc, RRKKctwftfinc, RRKKctwfvfinc, RRKKctwfwfinc, and RRKKctwfyfinc.

16. The peptide of claim 1 wherein said peptide is selected from RRKKcawftfinc, RRKKccwftfinc, RRKKcdwftfinc, RRKKcewftfinc, RRKKcfwftfinc, RRKKcGwftfinc, RRKKchwftfinc, RRKKciwftfinc, RRKKckwftfinc, RRKKclwftfinc, RRKKcmwftfinc, RRKKcnwftfinc, RRKKcpwftfinc, RRKKcqwftfinc, RRKKcrwftfinc, RRKKcswftfinc, RRKKctwftfinc, RRKKcvwftfinc, RRKKcwwftfinc and RRKKcywftfinc.

17. The peptide of claim 1 wherein said peptide is selected from RRKKcwwftfiac, RRKKcwwftficc, RRKKcwwftfidc, RRKKcwwftfiec, RRKKcwwftfifc, RRKKcwwftfiGc, RRKKcwwftfihc, RRKKcwwftfiic, RRKKcwwftfikc, RRKKcwwftfilc, RRKKcwwftfimc, RRKKcwwftfi pc, RRKKcwwftfiqc, RRKKcwwftfirc, RRKKcwwftfisc, RRKKcwwftfitc, RRKKcwwftfivc, RRKKcwwftfiwc, and RRKKcwwftfiyc.

18. The peptide of claim 1 wherein said peptide is selected from RRKKcwwftaiac, RRKKcwwftciac, RRKKcwwftdiac, RRKKcwwfteiac, RRKKcwwftGiac, RRKKcwwfthiac, RRKKcwwftiiac, RRKKcwwftkiac, RRKKcwwftliac, RRKKcwwftmiac, RRKKcwwftniac, RRKKcwwftpiac, RRKKcwwftqiac, RRKKcwwftriac, RRKKcwwftsiac, RRKKcwwfttiac, RRKKcwwftviac, RRKKcwwftwiac and RRKKcwwftyiac.

19. A pharmaceutical composition comprising the peptide of claim 1.

20. A method for treating influenza virus infection in a host animal, the method comprising administering a therapeutically effective amount of the peptide of claim 1 or a pharmaceutical composition comprising the peptide of claim 1 to the host animal.

* * * * *

UNITED STATES PATENT AND TRADEMARK OFFICE
CERTIFICATE OF CORRECTION

PATENT NO. : 10,538,554 B2
APPLICATION NO. : 15/778822
DATED : January 21, 2020
INVENTOR(S) : Mohamed Rajik Mohamed Ibrahim Page 1 of 1

It is certified that error appears in the above-identified patent and that said Letters Patent is hereby corrected as shown below:

In the Claims

In Claim 1, Column 111, Line 21, "A5 is f, h, n, or w." should read -- A5 is f, h, i, n, or w --.

Signed and Sealed this
Third Day of March, 2020

Andrei Iancu
*Director of the United States Patent and Trademark Office*